United States Patent

Mohrman et al.

(10) Patent No.: US 11,278,765 B2
(45) Date of Patent: Mar. 22, 2022

(54) METHODS AND APPARATUS FOR POWER EXPENDITURE AND TECHNIQUE DETERMINATION DURING BIPEDAL MOTION

(71) Applicant: Stryd, Inc., Boulder, CO (US)

(72) Inventors: Wyatt Mohrman, Boulder, CO (US); Kun Li, Boulder, CO (US); Gus Pernetz, Louisville, CO (US); James Williamson, Broomfield, CO (US); Li Shang, Boulder, CO (US); Robert P. Dick, Chelsea, MI (US)

(73) Assignee: Stryd, Inc., Boulder, CO (US)

( * ) Notice: Subject to any disclaimer, the term of this patent is extended or adjusted under 35 U.S.C. 154(b) by 762 days.

(21) Appl. No.: 15/463,261

(22) Filed: Mar. 20, 2017

(65) Prior Publication Data
US 2017/0189752 A1 Jul. 6, 2017

Related U.S. Application Data

(63) Continuation of application No. PCT/US2015/051181, filed on Sep. 21, 2015.
(Continued)

(51) Int. Cl.
*A63B 24/00* (2006.01)
*A61B 5/11* (2006.01)
(Continued)

(52) U.S. Cl.
CPC ........ *A63B 24/0006* (2013.01); *A61B 5/1118* (2013.01); *A61B 5/7271* (2013.01);
(Continued)

(58) Field of Classification Search
CPC ........ A63B 24/0062; A63B 2024/0065; A63B 2024/0068; A63B 2024/0071;
(Continued)

(56) References Cited

U.S. PATENT DOCUMENTS

| 5,043,692 A | 8/1991 | Sites et al. |
| 5,125,412 A | 6/1992 | Thornton |

(Continued)

FOREIGN PATENT DOCUMENTS

| CN | 202876289 | 4/2013 |
| DE | 10 2018 213 035 A1 | 2/2020 |

(Continued)

OTHER PUBLICATIONS

Chen, Diansheng, et al. "A wireless real-time fall detecting system based on barometer and accelerometer." 2012 7th IEEE Conference on Industrial Electronics and Applications (ICIEA). (Year: 2012).*

(Continued)

*Primary Examiner* — David J. McCrosky
(74) *Attorney, Agent, or Firm* — Cooley LLP

(57) ABSTRACT

Training at the proper level of effort is important for athletes whose objective is to achieve the best results in the least time. In running, for example, pace is often monitored. However, pace alone does not reveal specific issues with regard to running form, efficiency, or technique, much less inform how training should be modified to improve performance or fitness. A sensing system and wearable sensor platform described herein provide real-time feedback to a user/wearer of his power expenditure during an activity. In one example, the system includes an inertial measurement unit (IMU) for acquiring multi-axis motion data at a first sampling rate, and an orientation sensor to acquire orientation data at a second sampling rate that is varied based on the multi-axis motion data.

30 Claims, 13 Drawing Sheets

Related U.S. Application Data

(60) Provisional application No. 62/215,458, filed on Sep. 8, 2015, provisional application No. 62/053,205, filed on Sep. 21, 2014.

(51) Int. Cl.

| | |
|---|---|
| *G01C 21/16* | (2006.01) |
| *A61B 5/00* | (2006.01) |
| *A63B 69/00* | (2006.01) |
| *G01L 5/00* | (2006.01) |
| *G09B 19/00* | (2006.01) |

(52) U.S. Cl.
CPC ...... *A63B 24/0062* (2013.01); *A63B 69/0028* (2013.01); *G01C 21/16* (2013.01); *G01L 5/00* (2013.01); *G09B 19/0015* (2013.01); *G09B 19/0038* (2013.01); *A61B 2503/10* (2013.01); *A61B 2562/0219* (2013.01); *A63B 2024/0009* (2013.01); *A63B 2220/12* (2013.01); *A63B 2220/62* (2013.01); *A63B 2220/74* (2013.01); *A63B 2220/803* (2013.01); *A63B 2220/836* (2013.01); *A63B 2225/50* (2013.01); *A63B 2230/00* (2013.01)

(58) Field of Classification Search
CPC .... A63B 2220/10–16; A63B 2220/803; A63B 2220/836; A61B 5/1112; A61B 5/1113–1118; A61B 5/112–1124; A61B 5/1126; A61B 2562/0219; A61B 2503/10; G01C 21/005; G01C 21/16–165; G01C 22/00; G01C 22/006; G06K 9/00342
See application file for complete search history.

(56) References Cited

U.S. PATENT DOCUMENTS

| | | | |
|---|---|---|---|
| 5,899,963 A | 5/1999 | Hutchings | |
| 6,052,654 A | 4/2000 | Gaudet et al. | |
| 6,073,489 A | 6/2000 | French et al. | |
| 6,175,608 B1 | 1/2001 | Pyles et al. | |
| 6,464,485 B1 | 10/2002 | Iida et al. | |
| 6,493,652 B1 | 12/2002 | Ohlenbusch et al. | |
| 6,496,779 B1 | 12/2002 | Hwang | |
| 7,237,446 B2 | 7/2007 | Chan et al. | |
| 7,383,728 B2 | 6/2008 | Noble et al. | |
| D598,113 S | 8/2009 | Flaction et al. | |
| 7,634,379 B2 | 12/2009 | Noble | |
| 7,643,873 B2 | 1/2010 | Chan | |
| 7,753,861 B1 | 7/2010 | Kahn et al. | |
| 8,060,337 B2 | 11/2011 | Kulach et al. | |
| 8,157,707 B2 | 4/2012 | Flaction | |
| 8,655,618 B2 | 2/2014 | Flaction et al. | |
| 8,718,938 B2 | 5/2014 | Wolf | |
| 8,840,569 B2 | 9/2014 | Flaction et al. | |
| 9,433,843 B2 | 9/2016 | Morlock | |
| 9,888,868 B2 * | 2/2018 | Sarrafzadeh | A61B 5/6807 |
| 10,744,371 B2 | 8/2020 | Mohrman et al. | |
| 2005/0075586 A1 | 4/2005 | Jamsen | |
| 2007/0260418 A1 | 11/2007 | Ladetto et al. | |
| 2008/0288200 A1 | 11/2008 | Noble | |
| 2010/0211349 A1 | 8/2010 | Flaction et al. | |
| 2010/0292941 A1 | 11/2010 | Grasso | |
| 2010/0317489 A1 | 12/2010 | Flaction | |
| 2011/0022349 A1 | 1/2011 | Stirling et al. | |
| 2011/0207581 A1 | 8/2011 | Flaction | |
| 2011/0231101 A1 | 9/2011 | Bidargaddi et al. | |
| 2011/0313705 A1 | 12/2011 | Esser et al. | |
| 2012/0130673 A1 | 5/2012 | Dishongh | |
| 2012/0232430 A1 | 9/2012 | Boissy et al. | |
| 2013/0041617 A1 | 2/2013 | Pease et al. | |
| 2013/0053990 A1 | 2/2013 | Ackland | |
| 2013/0178958 A1 * | 7/2013 | Kulach | A61B 5/6807 700/91 |
| 2013/0190657 A1 | 7/2013 | Flaction et al. | |
| 2013/0190658 A1 | 7/2013 | Flaction et al. | |
| 2013/0338802 A1 | 12/2013 | Winsper et al. | |
| 2014/0277633 A1 | 9/2014 | Flaction | |
| 2014/0350703 A1 | 11/2014 | Flaction et al. | |
| 2015/0025817 A1 | 1/2015 | Kate et al. | |
| 2016/0313126 A1 | 10/2016 | Lemarchand et al. | |
| 2017/0074897 A1 | 3/2017 | Mermel et al. | |
| 2018/0043211 A1 | 2/2018 | Mohrman et al. | |

FOREIGN PATENT DOCUMENTS

| | | |
|---|---|---|
| EP | 2654030 | 10/2013 |
| WO | WO2007/008930 | 1/2007 |
| WO | WO2007/107491 | 9/2007 |
| WO | WO2008/143738 | 11/2008 |
| WO | WO2009/024600 | 2/2009 |
| WO | WO2010/046448 | 4/2010 |
| WO | WO 2012/071551 A1 | 5/2012 |
| WO | WO2015/075307 | 5/2015 |

OTHER PUBLICATIONS

Margaria, R., et al. "Energy cost of running." Journal of applied physiology 18.2 (1963): 367-370. (Year: 1963).*

Anastasopoulou, Panagiota, et al. "Using support vector regression for assessing human energy expenditure using a triaxial accelerometer and a barometer." International Conference on Wireless Mobile Communication and Healthcare. Springer, Berlin, Heidelberg. (Year: 2012).*

Ohtaki, Yasuaki, et al. "Automatic classification of ambulatory movements and evaluation of energy consumptions utilizing accelerometers and a barometer." Microsystem technologies 11.8-10 (2005): 1034-1040. (Year: 2005).*

U.S. Appl. No. 15/794,762, filed Oct. 26, 2017, Mohrman et al.

Bouten, C. V. et al., "Assessment of energy expenditure for physical activity using a triaxial accelerometer," *Official Journal of the American College of Sports Medicine*, pp. 1519-1523 (1994).

Estimate. (1992). In C. G. Morris (Ed.), Academic Press Dictionary of Science and Technology (4th ed.). Oxford, UK: Elsevier Science & Technology. Retrieved from https://search.credoreference.com/content/entry/apdst/estimate/0?institutionId=743, 2 pages.

Estimate. (2016). In Editors of the American Heritage Dictionaries (Ed.), The American Heritage Dictionary of the English Language (6th ed.). Boston, MA; Houghton Mifflin. Retrieved from: https://search.credoreference.com/content/entry/hm,dictenglang/estimate/0?instituionId=743, 2 pages.

International Search Report and Written Opinion dated Jan. 28, 2016 for International Application No. PCT/US15/51181, 14 pages.

Internet Archive. Xsens Website, "IMU Inertial Measurement Unit; Xsens3D motion tracking," Mar. 21, 2014. Retrieved from https://web.archive.org/web/20140321235531/http://www.xsens.com/tags/imu/, 3 pages.

Lindsey, J. Outside Online. "The Science Behind Styrd, the World's First Running Power Meter," May 27, 2015. Retrieved from https://www.outsideonline.com/1981811/science-behind-stryd-worlds-first-running-power-meter, 8 pages.

Non-Final Office Action dated Dec. 28, 2017 for U.S. Appl. No. 15/794,762, 16 pages.

Bouten et al., "Assessment of energy expenditure for physical activity using a triaxial accelerometer," Special Communications, Medicine and Science In Sports and Exercise, Aug. 1994,8 pages.

Omron Healthcare Inc., Omron Instruction Manual, Pocket Pedometer, 2010, 28 pages.

Partial Supplementary European Search Report dated May 3, 2018 for European Application No. 15841179.3, 14 pages.

Cooper, D. M. et al., "Aerobic parameters of exercise as a function of body size during growth in children," Journal of Applied Physiology, 56(3):628-634 (1984).

Final Office Action dated Jun. 20, 2018 for U.S. Appl. No. 15/794,762, 18 pages.

Umberger, B. R. et al., "A model of human muscle energy expenditure," Computer Methods in Biomechanics and Biomedical Engineering, 6(2):99-111 (2003).

(56) References Cited

OTHER PUBLICATIONS

Extended European Search Report dated Aug. 31, 2018 for European Application No. 15841179.3, 16 pages.
Non-Final Office Action dated Oct. 10, 2019 for U.S. Appl. No. 15/794,762, 10 pages.
Brodie, M. et al., "Fusion motion capture: a prototype system using inertial measurement units and GPS for the biomechanical analysis of ski racing," Sports Technol., 1(1): 17-28 (2008).
International Search Report and Written Opinion dated Oct. 29, 2020 for International Application No. PCT/US2020/40012, 11 pages.

* cited by examiner

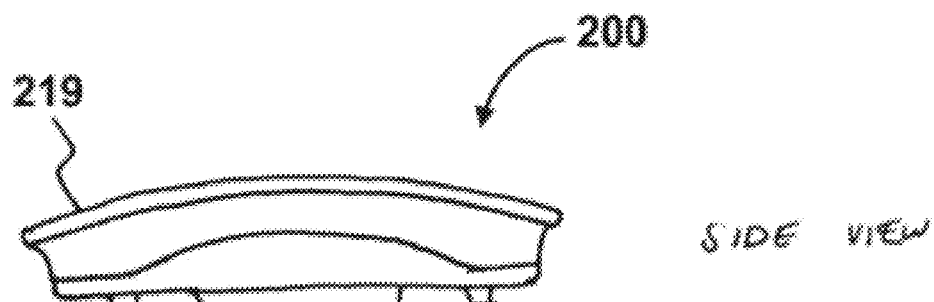
FIG. 2A  SIDE VIEW
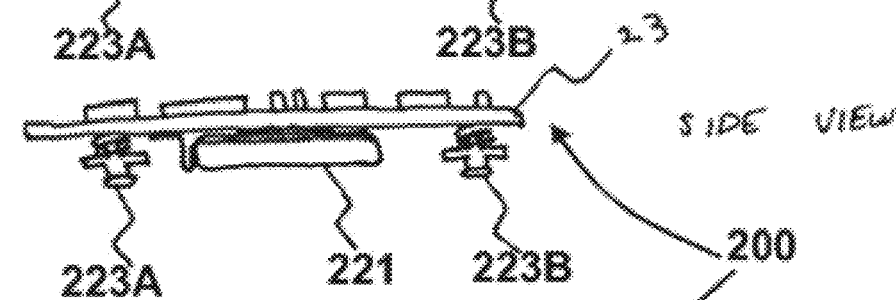
FIG. 2B  SIDE VIEW
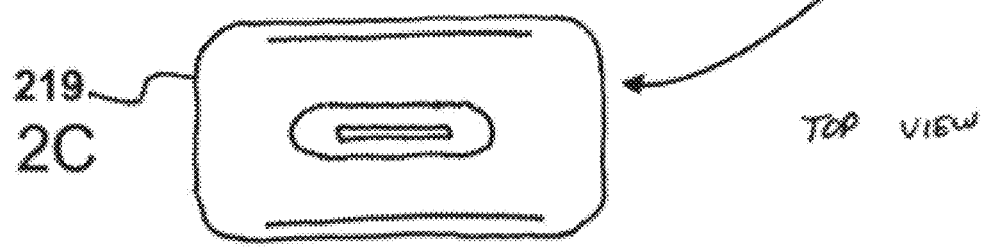
FIG. 2C  TOP VIEW
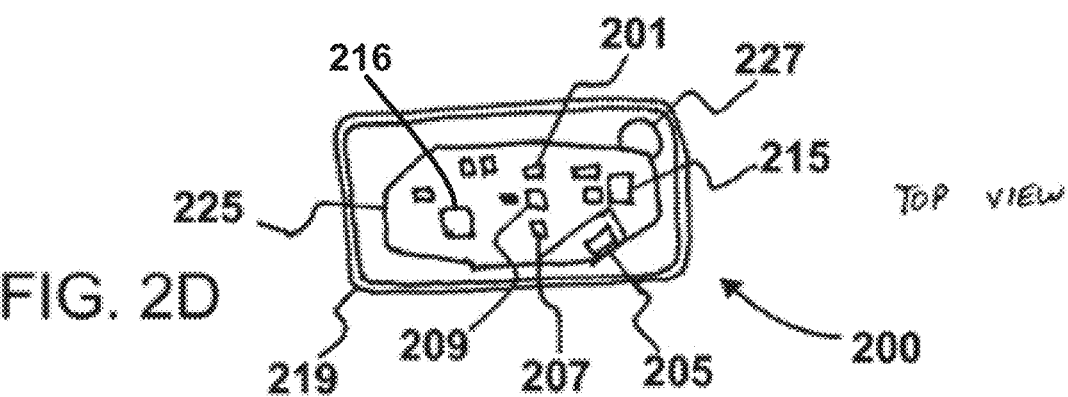
FIG. 2D  TOP VIEW

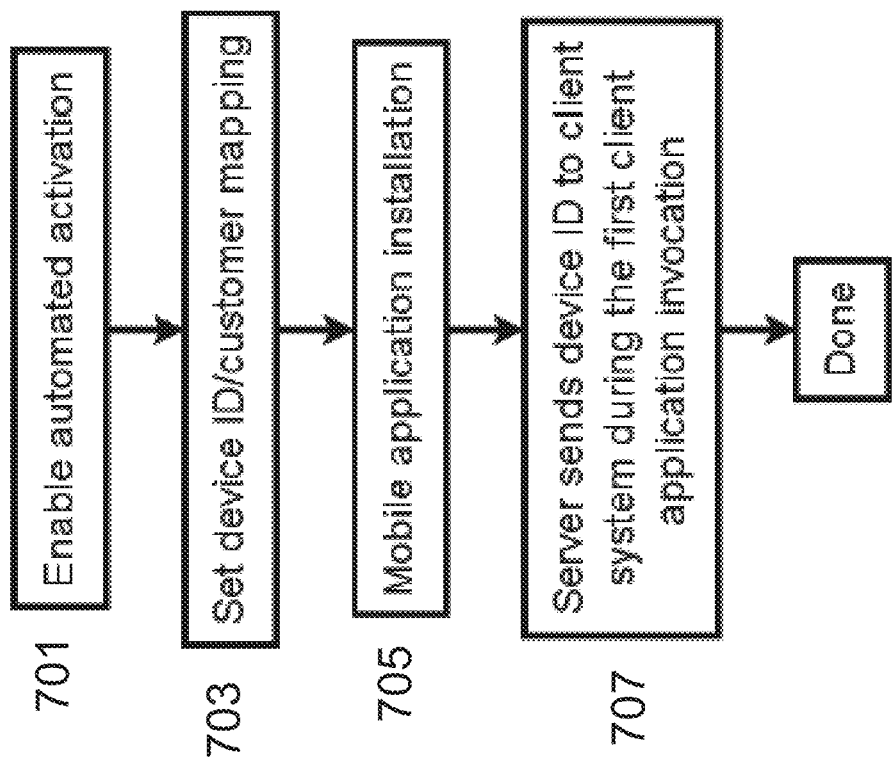

METHODS AND APPARATUS FOR POWER EXPENDITURE AND TECHNIQUE DETERMINATION DURING BIPEDAL MOTION

CROSS-REFERENCE TO RELATED PATENT APPLICATIONS

This application is a bypass continuation application of International Application No. PCT/US2015/051181, filed Sep. 21, 2015, entitled "Methods and Apparatus for Power Expenditure and Technique Determination during Bipedal Motion," which claims priority to U.S. Provisional Application No. 62/053,205, filed Sep. 21, 2014, titled "Power Expenditure and Technique Determination During Bipedal Motion," and claims priority to U.S. Provisional Application No. 62/215,458, filed Sep. 8, 2015, titled "Methods and Apparatus for Power Expenditure and Technique Determination During Bipedal Motion." Each of the foregoing applications is hereby incorporated herein by reference in its entirety.

BACKGROUND

Human activity can be classified based on comparisons between physiological and/or motion-related metrics and absolute thresholds. Sensors have been used to make measurements, based on which metrics are calculated. The current values of metrics are compared with absolute ranges to indicate whether adjustments are desired or needed. For example, a runner's heart rate metric might be compared with fixed thresholds and a warning produced if the metric varies outside a fixed range believed to be beneficial for training, competition, and/or recovery. In this case, the heart rate might be classified as inappropriately high, appropriate, or inappropriately low.

There exist methods of detecting signs of fatigue based on changes in heart rate. Such methods are unable to detect fatigue that results in deteriorating athletic form or technique due to changing properties of individual muscles.

There exist methods to measure physiological and/or motion-related data at fixed frequencies. High-frequency measurement results in high power consumption for battery-powered electronic systems, requiring large batteries or resulting in short battery lifespans.

There exist methods of measuring motion and position (and thus distance), such as via the Global Positioning System (GPS). These methods result in high power consumptions for battery-powered instantiations, limiting battery life or requiring large batteries. Existing methods of estimating changes in distance using lower-power sensors have been limited by error that increases with passing time and motion.

There exist methods of estimating the motion and positions of people engaging in bipedal motion, and the motion, positions, and orientations of their limbs. For example, Global Positioning System (GPS) technology can be used to determine the positions of people. However, this approach is prone to error in areas without access to satellite signal. Using this approach to estimate motion over short distance scales is error prone. In addition, this approach generally has high power consumption, resulting in short battery lifespans or large sizes for portable devices.

There are also techniques to estimate motion and positions of people using data from inertial measurement units fused with data from absolute or relative orientation measurement devices such as magnetometers or gyroscopes. Existing approaches are not capable of tracking positions and orientations of limbs for use in gait analysis. They are also prone to high power consumptions, resulting in short battery lifespans or large sizes for portable devices.

SUMMARY

Embodiments of the present disclosure include systems and methods for measuring motion of a user (e.g., an athlete) during a physical activity such as bipedal motion. In some embodiments, the system includes a housing and an inertial measurement unit (IMU) disposed within the housing for acquiring multi-axis motion data at a first sampling rate. The multi-axis motion can represent motion of the system in a reference frame fixed with respect to the housing. The system also includes an orientation sensor disposed within the housing to acquire orientation data at a second sampling rate, the orientation data representing an orientation of the system with respect to the Earth. A processor, disposed with the housing and operably coupled to the IMU and to the orientation sensor, can vary the second sampling rate based on the multi-axis motion data. A memory, disposed within the housing and operably coupled to the processor, can store the multi-axis motion data and the orientation data, and data interface, operably coupled to the processor, is configured to transmit the multi-axis motion data and the orientation data to another computing device.

In some embodiments, a method of estimating power expended by a user while wearing a sensor platform is described. The sensor platform includes an IMU and a memory, the memory configured to store (i) multi-axis motion data/measurements and (ii) orientation data/measurements. The multi-axis motion data represents motion measured by the IMU in a first reference frame fixed with respect to the sensor platform. The orientation data represents an orientation of the sensor platform in a second reference frame fixed with respect to the Earth. A communications link is established between a processor and the sensor platform. The sensor platform is caused to transmit the multi-axis motion data and the orientation data to the processor via the communications link. The processor translates the multi-axis motion data from the first reference frame to the second reference frame based on the orientation data so as to yield translated multi-axis motion data. The processor decomposes the translated multi-axis motion data into horizontal motion components and vertical motion components in the second reference frame. The processor estimates the power expended by the user based on the horizontal motion components and the vertical motion components.

In some embodiments, a method of measuring motion of a user during physical activity with a system comprising an IMU and an orientation sensor disposed within a housing, is described. The method includes: (1) acquiring multi-axis motion data with the IMU at a first sampling rate, where the multi-axis motion represents motion of the housing in a reference frame fixed with respect to the housing; (2) acquiring orientation data with the orientation sensor at a second sampling rate, where the orientation data represents an orientation of the housing with respect to the Earth; and (3) varying the second sampling rate based on the multi-axis motion data.

Some embodiments of the present disclosure relate to activity classification and providing feedback to those participating in and monitoring these activities, including automated methods of classifying and providing feedback on athletic activities. Some embodiments relate to determining the motion and/or positions of people engaging in bipedal motion, and/or the motion, positions, and/or orientations of their limbs, for example determining the power being produced by a human body during bipedal motion. Some embodiments of the present disclosure relate to the field of embedded sensing and signal processing hardware and software. For example, a wearable hardware-software system for sensing motion and other data, and analysis of these data to calculate metrics related to bipedal motion that can be used for on-line and off-line feedback to its user, are described.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 2A-2D are renderings of a sensor platform, according to some embodiments.

FIG. 7 shows an automated registration and activation process, according to some embodiments.

DETAILED DESCRIPTION

Figure 1A:
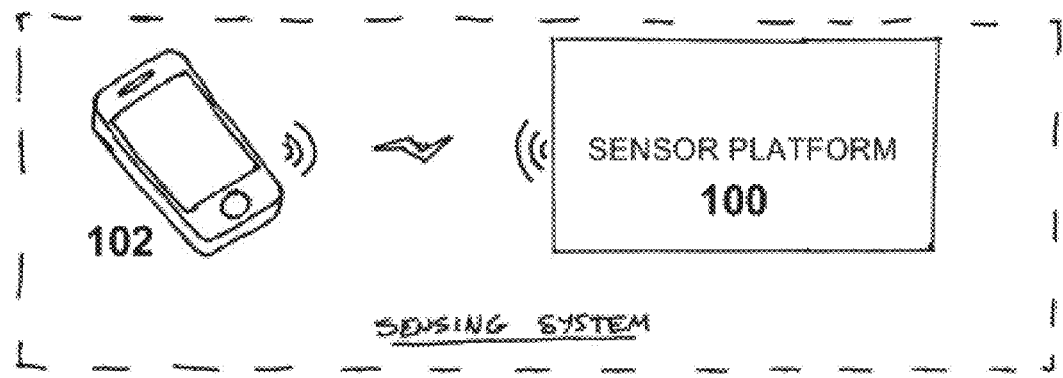
FIG. 1A shows a sensing system for sensing motion of a user during an activity, according to some embodiments.

Wearable sensor platforms and sensing systems described herein can sense motion and estimate power (i.e., mechanical power or biomechanical power) that a human body expends during physical activities such as running and other forms of bipedal motion. Training at the proper level of effort may be important for athletes whose objective is to achieve the best results in the least time. In running, for example, pacing (i.e., maintaining a desired speed) can be a useful metric to target, e.g., to improve endurance. However, pace alone is often not sufficient for achieving optimal or consistent results. For example, maintaining a runner's pace on hilly terrain can lead to early fatigue and/or reduced performance. Furthermore, measuring pace alone does not reveal specific issues with regard to running form, efficiency, or technique, much less inform how training should be modified to improve performance or fitness.

Embodiments of an inventive sensing system and wearable sensor platform described herein, however, sense motion and provide real-time feedback to a user/wearer of his power expenditure during an activity. By actively monitoring his power expenditure, an athlete can readily observe how changes in his technique (e.g., stride, body positioning, pace, cadence, etc.) impact his efficiency, and make adjustments to his technique accordingly, for example to minimize the power that he is expending. As such, through use of the sensor platform, the user will naturally modify his technique in ways that result in more efficient running forms, and that reduce the "wear and tear" experienced by his body during the activity. Also, using the example of the running scenario noted above, by targeting or maintaining a desired power expenditure (instead of a pace) on hilly terrain, the user can achieve faster overall times on a course by redistributing his effort and avoiding premature fatigue. Furthermore, by monitoring his capacity to produce and sustain power, an athlete can better assess his fitness level, as well as monitor how his training is affecting his fitness level over time.

Embedded hardware/software sensing systems of the present disclosure use a variety of signal processing techniques to calculate activity-specific metrics of merit for those involved in bipedal activities, such as walking, running, dancing, and/or the like. To provide a user with customized, automated and/or manual advice on physical activity, time-dependent distributions of physiological and/or motion-related metrics for a user are measured/sensed by the sensor platform, and used to inform automated and manual advice that is provided to the user via the sensing system. Applications of the present disclosure include reducing injury risk, improving athletic performance, improving the benefits of training sessions, enabling physical collaboration, and enabling motion-based control over other devices.

Functionalities of the disclosed system can include: (1) measuring physiological and motion-related data with one or more sensors (e.g., within a sensor platform), each of which may have one or more sensors as well as wired or wireless communication interfaces; (2) computing metrics of interest based on these data, either on the same module that gathered the data or after wired or wireless transmission to another module; and/or (3) displaying metrics of interest (e.g., via a user interface) to users of the system and providing advice on how to change their activity, form, or technique to achieve better training, competition, and/or recovery results.

These functionalities may be distributed across different physical modules, some of which may be computing/communication devices from third parties, such as smart phones, smart watches, and/or other computing devices. They may also be integrated into one or more physical modules. For example, any of the functionalities described herein may be performed within the sensor platform, within a mobile device that is separate from the sensor platform (e.g., a smart phone in wireless communication with the sensor platform), or shared between the sensor platform and the mobile device.

Wearable Sensor Platform—Physical Description

Sensing devices (or "sensor platforms") of the present disclosure can include multiple sensors, such as inertial measurement units (IMUs, such as accelerometers (e.g., one-axis, two-axis or three-axis accelerometers), gyroscopes, and magnetometers), temperature sensors, inertial sensors, force sensors, pressure sensors, Global Positioning System (GPS) receivers, and flex sensors, as well as local digital and analog signal processing hardware, storage device(s), energy source(s), and wireless transceivers integrated into apparel and/or wearable accessories relevant to bipedal motion, such as shoes, insoles, socks, leg bands, arm bands, chest straps, wrist bands/bracelets, and/or the like. Some of the aforementioned sensors, such as accelerometers, gyroscopes and magnetometers, can function as orientation sensors. The sensor platform may contain or be attached/operably coupled to more than one sensor of each type. Additional interface devices and computation devices capable of communicating with the sensor platform may also be used.

FIG. 1A shows an exemplary sensing system for sensing motion of a user, in which a sensor platform 100 is configured to wirelessly communicate with a mobile device 102 (e.g., a smart phone) and/or a communications network via a wireless communications link (e.g., using one or more RF protocols such as Bluetooth LE, Bluetooth, Wi-Fi, and/or Zigbee). In some embodiments, the sensor platform is also configured for wired communication (e.g., via an Ethernet cable, universal serial bus (USB), etc.) with the mobile device 102, personal computer, tablet, and/or the like.

Figure 1B:
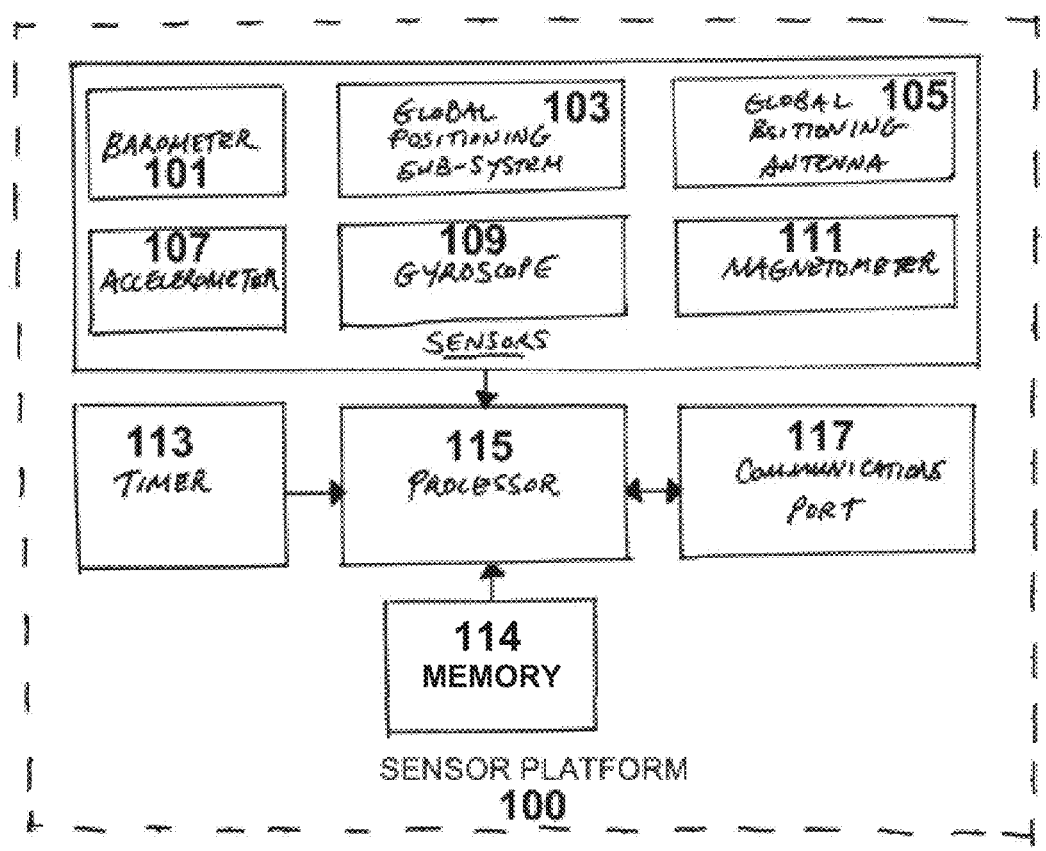
FIG. 1B is a block diagram of a sensor platform, according to some embodiments.

FIG. 1B is an example block diagram of the sensor platform 100 of FIG. 1A, in which a collection of sensors (barometer 101, Global Positioning System (GPS) subsystem 103 (e.g., including a GPS receiver), global positioning antenna 105, accelerometer 107, gyroscope 109, and magnetometer 111) and a timer 113 are electrically coupled to a processor 115, configured to send/receive signals via a communications port 117. Instead of, or in addition to, barometer 101, any other type of pressure sensor (e.g., atmospheric pressure sensor, air pressure sensor, pressure altimeter, and/or the like) can be used. The barometer 101 or other pressure sensor can measure/sense changes in pressure, for example as the user is moving. These changes in pressure can, in turn, be used by the sensing system to determine changes in the user's elevation, wind speed, running form, aerodynamics (which can change, e.g., due to changes in environmental conditions, physiological state of the user, the user's apparel/footwear, etc., over time as well as from activity to activity). The GPS subsystem 103 can acquire, via the global positioning antenna 105, a GPS signal including a user's geolocation (e.g., including latitude, longitude, altitude, and the current time). The accelerometer 107 can be a single-axis, two-axis, or three-axis accelerometer. Instead of, or in addition to, accelerometer 107, any other type of inertial measurement unit (IMU) (e.g., gyroscope, magnetometer, and/or the like) can be used. The accelerometer 107 or other IMU can measure/sense magnitude and direction of "proper acceleration" (physical acceleration), velocity, and/or orientation of a user. The gyroscope 109 (e.g., a MEMS gyroscope) can measure the orientation with respect to a fixed axis, and/or the angular velocity, of a user. The magnetometer 111 (e.g., a magnetoresistive permalloy sensor) can measure the orientation of a user with respect to the Earth's magnetic field. Since each of the accelerometer 107, the gyroscope 109, and the magnetometer 111 is capable of measuring orientation, one or more can be omitted from some designs of the sensor platform. For example, in cases where an accelerometer is being used to determine orientation, a separate gyroscope 109 and/or magnetometer 111 may not be included in the sensor platform. True net acceleration in physical space can include both linear acceleration (e.g., as measured by an accelerometer) and angular acceleration (e.g., as measured by a gyroscope). The timer 113 can provide time data (e.g., time stamps corresponding to historical measurements taken by sensors of the sensor platform 100). Time data can be stored locally (e.g., in a memory 114), used by the processor 115 for computation of one or more metrics of interest described herein, and/or transmitted via the communications port 117 (e.g., along with other measurement data derived directly from the sensors of the sensor platform 100 or stored in memory 114) to a mobile device (e.g., smart phone 102) or other remote processing device, e.g., over a communications network. In some cases, the communications port 117 includes, or is replaced by, a "data interface" which can include an antenna, an Ethernet connection, a USB port, or any other wireless or wired interface to facilitate communication (and transfer of data) between the sensor platform and a remote device (e.g., a mobile device, a communications network, etc.).

In some implementations, signal processing and feature extraction is completed via one or more algorithms running on one or more processors (e.g., processor 115). The signal processing and feature extraction can be performed partially on the sensor platform (e.g., sensor platform 100, which can be an apparel-embedded or athletic accessory-embedded portion of the sensing system) and may also be completed partially on a processing device (e.g., mobile device 102 or other device in wireless communication with the sensor platform). In other implementations, the sensor platform 100 transmits raw data (once measured/collected and/or stored in memory 114) to a remote processing device (e.g., mobile device 102 or other device in wireless communication with the sensor platform), either autonomously (e.g., according to a delivery schedule) or in response to a request received at the sensor platform from the remote processing device, for example by RF communications over a wireless communications link established by the communications port of the sensor platform, or via a wired connection (e.g., Ethernet) such that the remote processing device performs the signal processing. Information can be provided to the user (1) partially by the sensor platform and partially by a mobile device; (2) primarily or exclusively by the sensor platform (e.g., sensor platform 100); or (3) primarily or exclusively by the mobile device (e.g., mobile device 102).

A user interface and a computation device may reside within the same device, e.g., within mobile device 102, or in the sensor platform 100 itself, or may be housed separately (e.g., a computation device or processor within the sensor platform and a user interface in a mobile device, or vice-versa). A server (e.g., one or more remote servers, "the cloud," etc.) may also be used for additional analysis of data gathered by the sensor platform 100. A single server may gather data from one or more sensor platforms 100. Data may be transmitted from the sensor platform 100 to the server via a proxy, such as a computation device.

FIGS. 2A-2D are renderings of a sensor platform 200, according to some embodiments. The sensor platform 200 can be used, for example, as part of a sensing system (e.g., as sensor platform 100 in FIG. 1A). FIG. 2A is a side view of an assembled sensor platform 200, in which an enclosure or "housing" 219 and two metal snaps 223A, 223B are visible. FIG. 2B is a side view of a partially disassembled sensor platform 200, in which a battery 221 and two metal snaps 223A, 223B are visible. FIG. 2C is a top view of an assembled sensor platform 200, showing enclosure 219. FIG. 2D is a top view of a partially disassembled sensor platform 200, in which a portion of the enclosure 219, a printed circuit board 225, a vent 227, an accelerometer 207, a gyroscope 209, a barometer 201, a microcontroller (or "processor") 215 operably coupled to a memory 216, and an antenna 205 are visible. The metal snaps 223A, 223B can be used to mechanically and/or electrically couple the sensor platform 200 to a garment (e.g., a shirt, shorts, arm band, leg band, shoe, etc.) or an accessory (e.g., a chest strap, arm band, leg band, watch, wrist band. bracelet, and/or the like) so that the sensor platform 200 is in close proximity with, or in contact with, the user's body.

In some examples, the processor 215 is configured to: (1) translate multi-axis motion data, using orientation data (e.g., measured by the accelerometer 207 and/or the gyroscope 209), from the reference frame fixed with respect to the housing 219 to a reference frame fixed with respect to the Earth so as to yield translated multi-axis motion data; (2) decompose the translated multi-axis motion data into horizontal motion components and vertical motion components in the reference frame fixed with respect to the Earth; and (3) estimate power expended by the user based on the horizontal motion components and the vertical motion components.

The memory 216 can store previously measured multi-axis motion data, and the processor 215 can be configured to vary the first sampling rate based on a comparison of the motion data to the previously measured multi-axis motion data.

The sensor platform 200 or sensing system (e.g., of FIG. 1A) can include a pressure sensor (e.g., an atmospheric pressure sensor or air pressure sensor, such as barometer, operably coupled to a processor. For example, as shown in the sensor platform 200 of FIG. 2D, barometer 201 is operably coupled to the processor 215 via PCB 225, to measure changes in pressure experienced by the system due to variations in altitude and/or wind resistance. Alternatively or in addition, the sensor platform or sensing system can include a Global Positioning System (GPS) receiver (e.g., of GPS subsystem 103 in FIG. 1A), operably coupled to the processor 215, to receive a GPS location signal representing a location of the system. The sensor platform 200 can also include a flexible potting compound (see, e.g., discussion of FIG. 4 below), disposed within the housing 219, to reduce mechanical stress experienced by at least one of the housing 219, the IMU (e.g., accelerometer 207), and the orientation sensor (e.g., gyroscope 209), and/or other components of the sensor platform 200 whose performance can be affected by excessive mechanical stress, e.g., due to impact forces during running, vibration, etc.

Figure 3A:
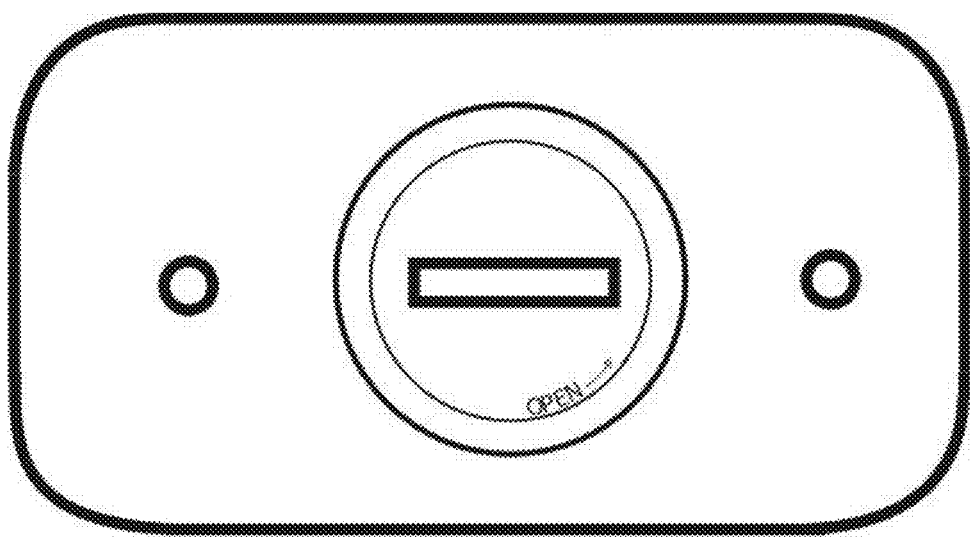
FIGS. 3A and 3B are renderings of top and bottom views, respectively, of an assembled sensor platform, device according to some embodiments.
Figure 3B:
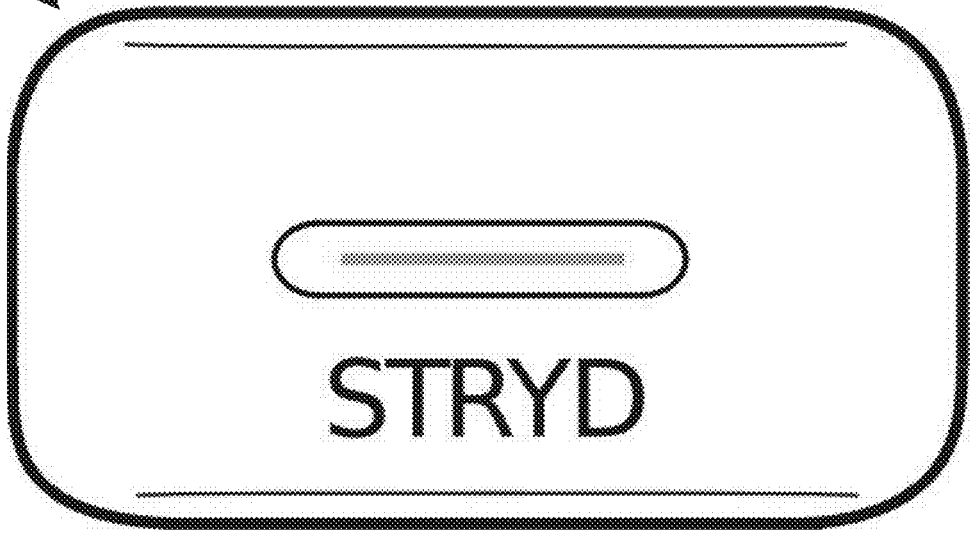
Figure 3C:
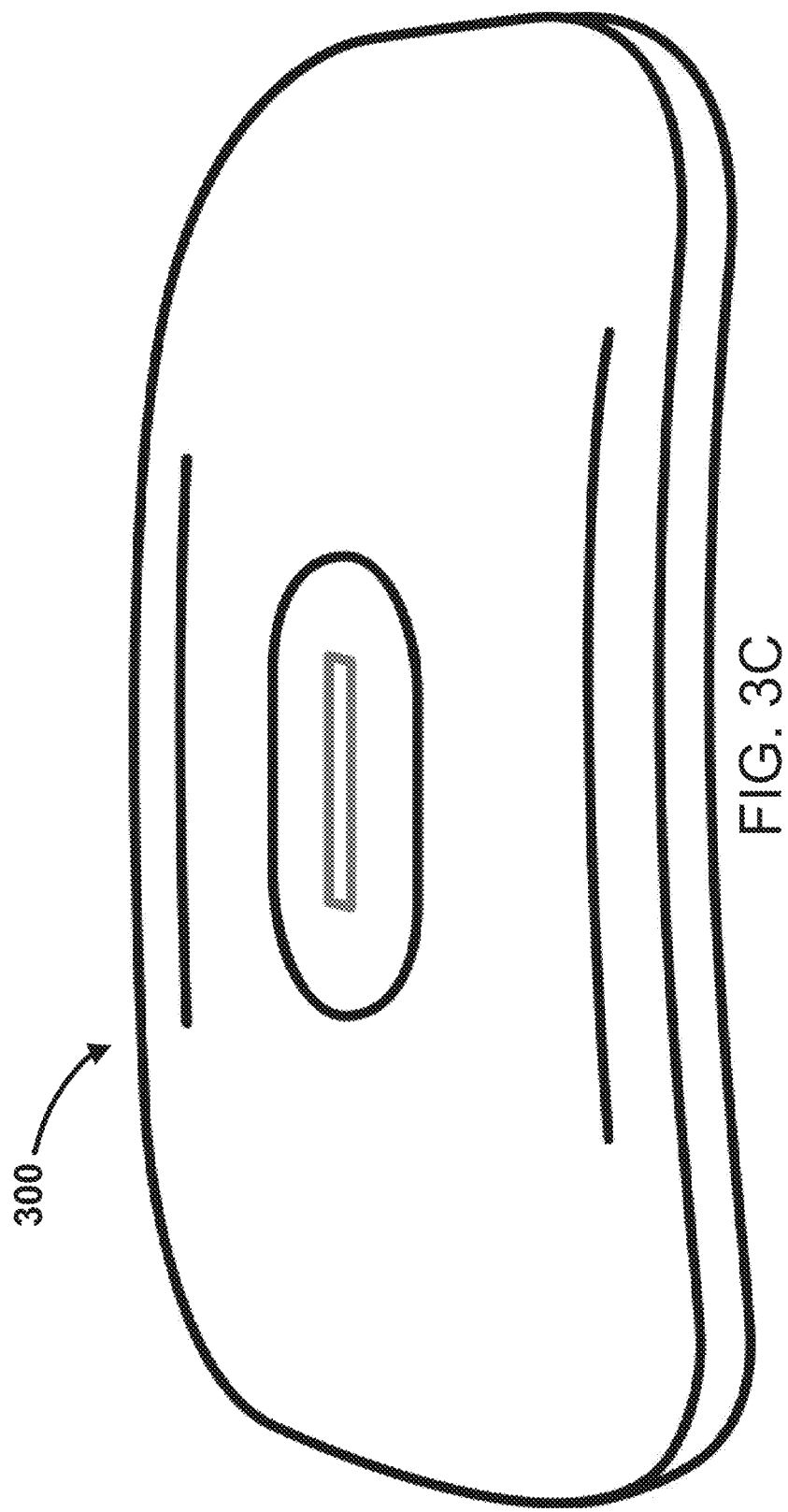
FIG. 3C is a rendering of a top perspective view of the assembled sensor platform of FIGS. 3A and 3B.

FIGS. 3A and 3B are renderings of top and bottom views, respectively, of an assembled sensing platform 300 according to some embodiments, and FIG. 3C is a rendering of a top perspective view thereof. The sensor platform 300 can be used, for example, as part of a sensing system (e.g., as sensor platform 100 in FIG. 1A). As shown in FIG. 3A, the sensing platform enclosure or housing can include a replaceable cover coupled (e.g., threadably) to the housing, that a user can rotate for removal, e.g., to allow the user access to the internal power source (e.g., a coin cell battery) for replacement. The profile of the sensing platform housing, as shown in FIGS. 3A-3C, can have a smooth, contoured profile and compact form factor to facilitate integration into a wearable electronics garment and/or for attachment to a garment or accessory. Two holes (shown in FIG. 3A) can be provided for mechanical and/or electrical attachment to the garment or accessory (e.g., via snap engagement).

Figure 4:
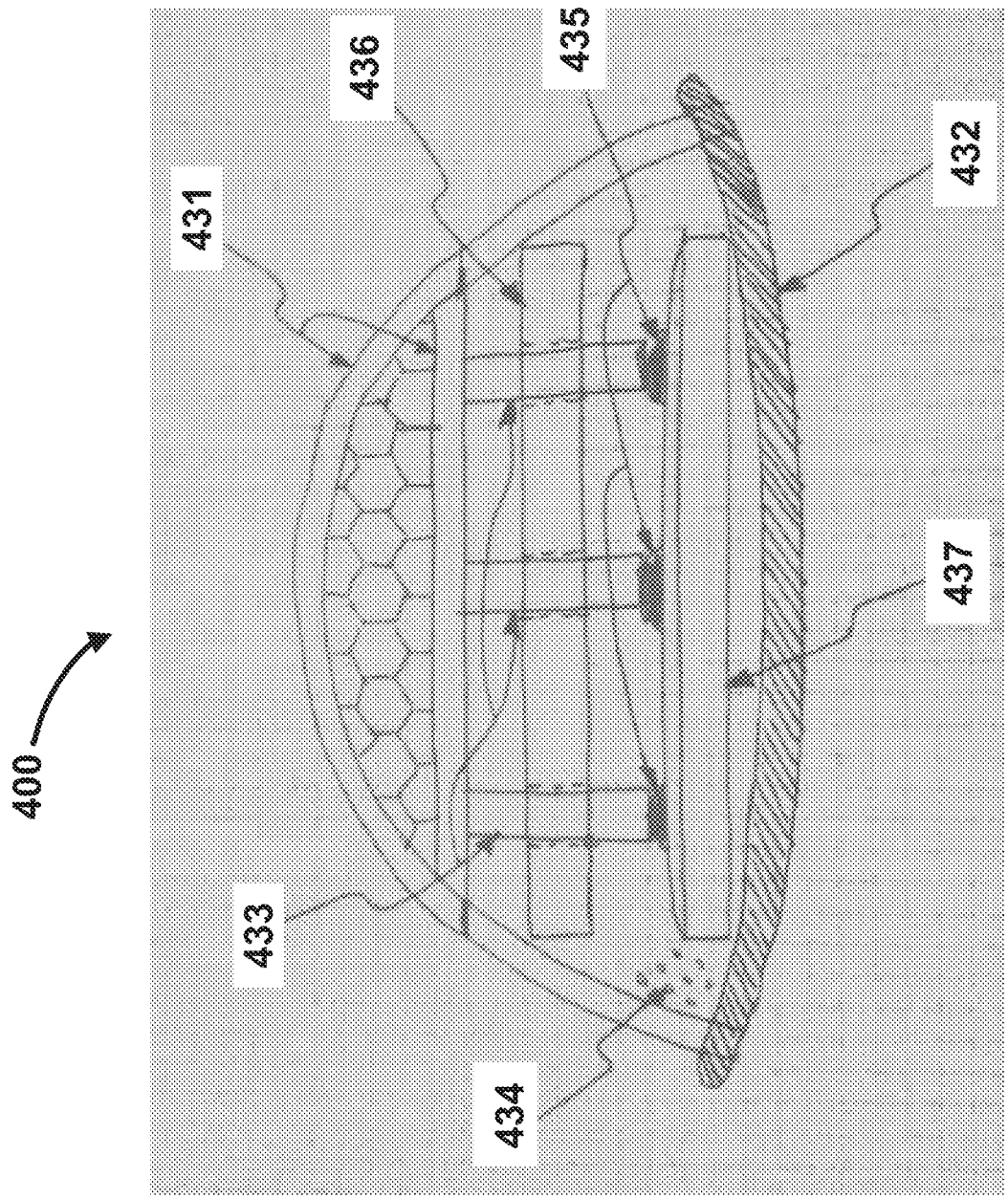
FIG. 4 shows a sensor device enclosure for harsh environments, according to some embodiments.

FIG. 4 shows a sensor platform 400 with an enclosure (also referred to herein as a "housing" or "package") for harsh environments, according to some embodiments. The sensor platform 400 can be used, for example, as part of a sensing system (e.g., as sensor platform 100 in FIG. 1A). In some implementations, the enclosure of the sensor platform 400 may be embedded in a piece of apparel (e.g., in an athletic shoe, a shirt, shorts, etc.) or an athletic accessory (e.g., a chest strap, arm band, leg band, wrist band, headband, watch, smartphone, dongle, and/or the like) that is, or will be during use, subject to high forces, and as such may include one or more features (such as those shown in FIG. 4) to promote durability and/or to protect the embedded electronics of the sensor platform 400.

The sensor platform enclosure can be a high-performance, robust enclosure for protecting embedded electronics. For example, the sensor platform 400 enclosure as shown in FIG. 4 includes an arched top 431, a reinforced bottom plate 432, a plurality of weight distribution pillars 433 to distribute forces (e.g., impact, vibration, etc.) experienced by the sensor platform, a flexible potting compound 434, a plurality of shock absorbers 435 each disposed at an end of a corresponding weigh distribution pillar, a printed circuit board (PCB) 436, and a battery 437 (e.g., a coin cell battery).

To protect any flex-sensitive areas of the embedded circuitry, and to protect against breakage of solder joints between integrated circuit (IC) packages and printed circuit boards (PCBs), a package/enclosure (e.g., including arched top 431 and/or bottom plate 432) with structural rigidity can be used. To allow for an unrestricted, or less restricted, natural movement of the user's foot while in the shoe and under movements desired or needed while running, the enclosure (e.g., including arched top 431 and/or bottom plate 432) can include flexible sections placed in areas mirroring the points of flex, e.g., joints of the human foot.

During running or walking, the bottom side of the shoe can experience forces that are both high in pressure and confined to small spatial areas. Some examples include stepping into a curb corner, an upturned rock, upturned metal bolt, or any other often accidentally-encountered debris. Such forces pose a risk to embedded circuitry through either extreme torsion (e.g., possibly damaging solder joints), or other types of damage, such as punctures. As such, the enclosure (e.g., including arched top 431 and/or bottom plate 432) can include a puncture-resistant material.

A shoe with embedded circuitry can include protection against accumulated water, dirt, and sweat encountered over the life of the shoe. For example, the enclosure (e.g., including arched top 431 and/or bottom plate 432) can include a watertight or water-resistant material.

A shoe with wirelessly connected embedded circuitry can include an enclosure that will not impair the RF performance of its wireless antenna. In such embodiments, metallic and other conductive materials may not be used on the upper portions of the enclosure (e.g., arched top 431) which may otherwise impair wireless antenna signal strength.

The density of the enclosure (e.g., including arched top 431 and/or bottom plate 432), in some embodiments, is designed so as not to exceed the density of the surrounding shoe materials, thereby adding little or no extra weight as compared with a shoe without embedded circuitry. In some embodiments, the enclosure size is kept small while increasing or maximizing structural support to provide high performing load-bearing and shock-absorption capabilities.

The sensing device enclosure can also include one or more of the following:

The package/enclosure (e.g., including arched top 431 and/or bottom plate 432) can include both rigid and flexible materials, each of which may be both light in weight ("lightweight") and have high strength ("rugged"). Rigid materials can include lightweight yet high-strength Kevlar® plastics or woven carbon fibers. Flexible materials can include flexible potting compounds, foams, and fabrics.

Vertical enclosure walls of the package/enclosure (e.g., including arched top 431 and/or bottom plate 432) can be reinforced. For example, the enclosure walls can be made thicker by additional impregnation of high strength materials throughout in designs advantageous for increased load-bearing performance (e.g., in a weight-saving honeycomb structure).

The top (foot-facing) side of the enclosure can have a curved arch shape (e.g., also placed with and following the contours of the human arch) to distribute the weight of the user directly and evenly into each reinforced load-bearing structure of the enclosure. Honeycombed bridge-like supports connect the arch top with the reinforced walls for extra weight-bearing and shock-absorbing capability. Sensor platform 400 of FIG. 4, for example, includes a top arch/exterior wall 431.

The package/enclosure (e.g., including arched top 431 and/or bottom plate 432) may employ a reinforced flat plate (e.g., reinforced bottom plate 432 in FIG. 4) for added toughness/durability on the road-facing side of the shoe. The reinforced plate can include materials such as metal plate or other high-strength materials, e.g., made from synthetic fibers such as Kevlar® plastics and woven carbon fiber. The reinforced plate can be sized to match the areas of circuitry it is intended to protect, and can be cut into sections that link together so as not to compromise the overall flexibility performance of the shoe. It can be attached to the main package itself through an epoxy resin bonding process, e.g., prior to or during the shoe manufacturing process.

Multiple cylindrical pillars (e.g., load-bearing weight distribution pillars 433 of FIG. 4) can be placed/positioned so as to extend vertically from the arched top through holes cut in the PCB (e.g., PCB 436 in FIG. 4) and down to the coin cell battery (e.g., battery 437 in FIG. 4) underneath the PCB. The pillars can thus be configured to transfer applied stresses from the top of the arch or, alternatively, from the reinforced bottom plate, to completely bypass the embedded circuitry. The bottoms of the pillars can be positioned so that they rest against resin or rubber shock absorbers (e.g., shock absorbers 435 of FIG. 4) disposed between the pillars and the coin battery.

The package/enclosure of the sensor platform 400 can include flexible sections to allow movement of the enclosure with the natural movement of the shoe under scenarios, such as normal walking, running, and/or sports playing. Such flexible sections can be made of flexible materials such as rubbers and resins, and can be attached in the area between the enclosure bottom and the reinforced bottom plate 432.

A flexible, non-conductive epoxy resin (or "potting compound") can be used to partially or entirely fill the package/enclosure (e.g., as defined between the arched top 431 and the bottom plate 432) containing both circuitry and battery. The flexibility of the resin can aid in shock absorption to buffer and neutralize mechanical stresses applied to the enclosure. The potting compound can also provide water-tight protection from water, dirt, and sweat, while also protecting the circuitry from unnecessary access and/or tampering by the user. The sensor platform 400 of FIG. 4, for example, includes a flexible potting compound 434.

As described herein, a system for measuring motion of a user during physical activity can include a housing and an inertial measurement unit (IMU) disposed within the housing to acquire multi-axis motion data at a first sampling rate. In such cases, the multi-axis motion represents motion of the system in a reference frame fixed with respect to the housing. An orientation sensor (e.g., an accelerometer, gyroscope, or magnetometer) is also disposed within the housing, and configured to acquire orientation data at a second sampling rate. In some cases, the IMU itself (e.g., when the IMU is an accelerometer) serves as an orientation sensor by sensing the direction of weight changes of the user. The orientation data represents an orientation of the system, for example with respect to the Earth. A processor is disposed within the housing and operably coupled to the IMU and to the orientation sensor, to vary the second sampling rate based on the multi-axis motion data. A memory, disposed within the housing and operably coupled to the processor, is configured to store the multi-axis motion data and the orientation data. A data interface, operably coupled to the processor, is configured to transmit the multi-axis motion data and the orientation data to another computing device.

Reinforcements can be made to the system packaging as described above with reference to FIG. 4. For example, the housing can include an arched wall (e.g., arched top wall 431), a reinforced plate (e.g., reinforced bottom plate 432) disposed opposite the arched wall, and a plurality of weight distribution pillars (e.g., weight distribution pillars 433) between the arched wall and the reinforced plate.

In some configurations, the orientation sensor comprises a gyroscope. The memory can store previously measured multi-axis motion data, and the processor can be configured to vary the second sampling rate based on a comparison of the multi-axis motion data to the previously measured multi-axis motion data. The processor can also be configured to (i) estimate when the user is airborne based on the multi-axis motion data and (ii) disable the gyroscope when the user is airborne.

Use of the Wearable Sensor Platform

Figure 5:
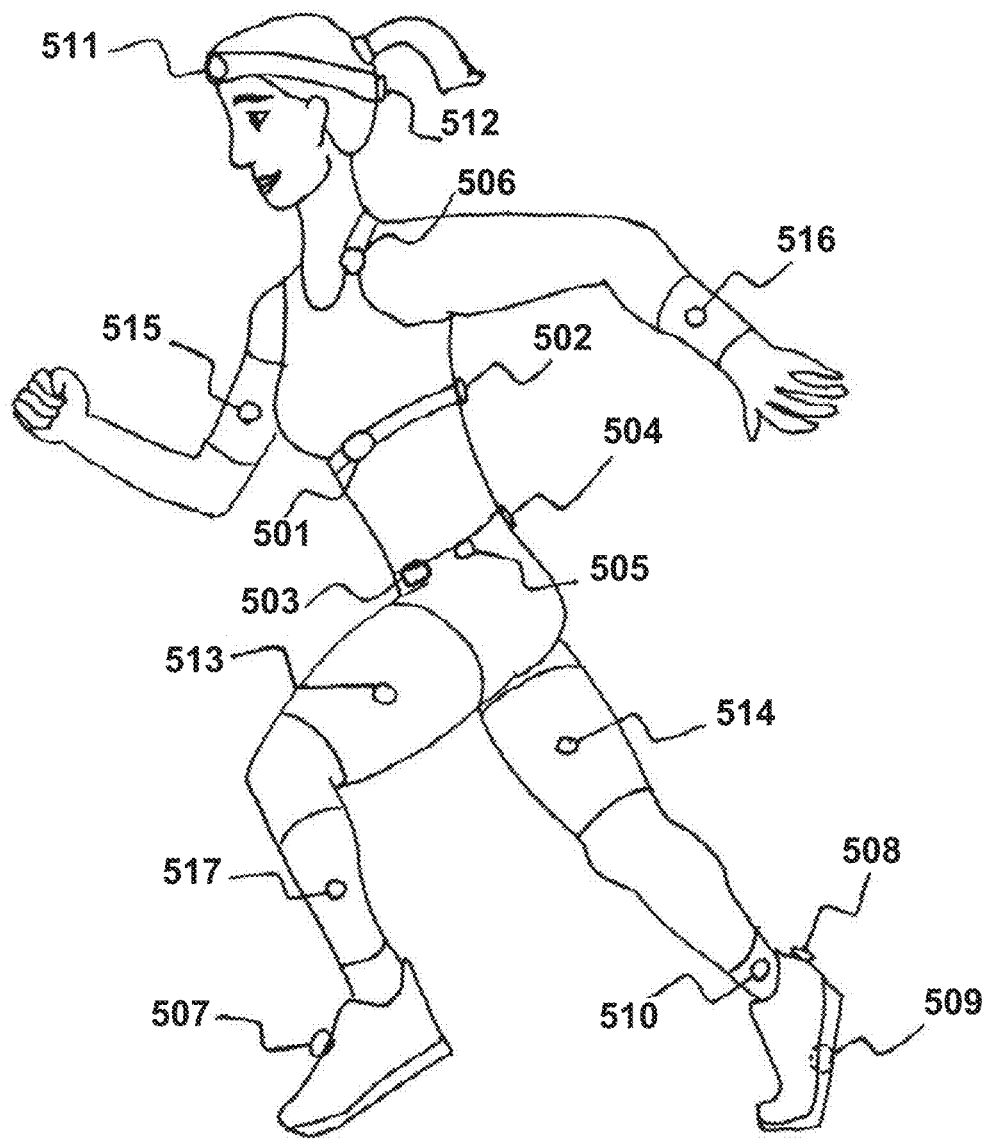
FIG. 5 shows the placement of components of a sensing system on a user, according to some embodiments.

During use, a user affixes a sensor platform as described herein (e.g., sensor platform 100 of FIG. 1A) to a surface of, or in close proximity to, his body (e.g., secured by a chest strap, wrist strap, leg band, etc.) and conducts a physical activity such as walking, running, dancing, and/or the like. By way of example, the sensor platform (e.g., including one or more inertial measurement units, an orientation sensor, and an optional barometer) may be placed on various locations of the body, for example, at the following locations, as shown in FIG. 5: on the front 501, back 502, or side of the torso, on the front 503, back 504, or side 505 of the waist, embedded in clothing 506, attached to (507, 508) or embedded within (509) one or both shoes, on one or both socks 510, on the front 511 or back 512 of a headband, on one or both thighs (513, 514), in one or both arm bands (515, 516), or on one or both calves 517. Depending upon the implementation, each location can have one or more of the following advantages: (a) convenience to the user, (b) accuracy of measuring running and/or walking technique and distance, (c) accuracy in measuring the geographic position of the user, (d) improved sensed data quality, (e) improved user comfort, (f) monitoring of one or more limbs of a user; and (f) reduced stress on the sensing device. By way of example, beneficial locations can include within or on a strap attached to the ankle, leg, wrist, waist, or torso. The sensor platform can also be placed within or on apparel such as clothing, belts, or shoes. It can also be placed on, under, or to the side of the foot.

To control cost and/or setup time, a limited number of sensing devices can be used per person or group. For example, in some situations, it may be difficult or impractical to monitor more than one limb, and the estimation accuracy enabled by such data may differ depending on limb. In such cases, the sensing device(s) can be placed on the limb enabling more accurate estimation(s) of metrics of interest.

The sensor platform can include a user interface (e.g., including an electronic display, touchscreen, pushbuttons, dials, indicator light(s), speaker(s), microphone(s), keyboard, etc.), for example to allow users access to information about metrics and maps described herein. In some embodiments, the user interface functionality is divided between/among the sensor platform, and software running on a mobile device (e.g., commodity or special-purpose devices, such as smartphones) that communicates with the sensor platform. In some embodiments, the user interface functionality resides within a mobile device. In some embodiments, the user interface functionality resides within the sensor platform. The device that contains the user interface (e.g., the mobile device 102 and/or the sensor platform 100 of FIG. 1A) may be called an "interface device."

The sensor platform can provide feedback to a user in audio-visual form during use. The sensor platform and user interface can provide off-line and real-time information to the users. The real-time information can be easy to access, and accessible during physical or mental activity. For example, a compact colored light on the sensor platform, or audio output from the user interface, may be used to indicate information to a user. In some embodiments, the off-line information is organized to allow users to vary the level of detail and type of information displayed. For example, users may scroll through a map or timeline of activities to see detailed information about metrics of interest for different times and locations. The system may also be prompted to provide information of interest that did not originate in the sensor platform, e.g., metrics of interest from other users, the time, and personal information stored on the interface device (e.g., a smartphone).

Feedback Triggering

The sensor platform and/or interface device can provide active and/or passive feedback to the users. Active feedback has the potential to distract the user from physical or mental activities, and can be presented on a schedule chosen by the user, when explicitly requested, or when determined to be valuable due to values or patterns in metrics of interest. Users may explicitly request active feedback through actions that require little deviation from their ongoing activities, e.g., by a gesture such as tapping a foot, changing the angle of a limb, or tensing a particular muscle.

Persistent Audio Feedback Using Rhythm and Tone

Feedback about metrics of interest, e.g., impact timing and intensity, may be provided via subtle changes in the rhythm, harmony, and dissonance of automatically generated music, or through automatic changes in music recordings or media references provided by the user. The feedback can be adjusted and synchronized to motion patterns of the user. For example, subtle notes can be played to direct the user toward the ideal cadence. For example, when an activity such as running starts, another bass or drumbeat sound can be joined/added. The background beat can naturally adjust phase to match that of the athlete's steps, and/or adjust period to be slightly closer to the ideal than the user's current cadence. As the user adjusts cadence slightly in the right direction, the background beat can take another step towards the optimal. When the user hits the optimal cadence, both beats can overlap. The notes for the beats can be harmonic. The athlete footstep beat can be composed of two notes. They can be harmonic when other efficiency metrics are well optimized. Otherwise, they can be dissonant. Different tones, degrees of harmony, and tone durations can be used to provide information about multiple metrics of interest.

A variant of this interface technique is to modify parameters of music provided by the athlete. For example, a piece of music with appropriate initial tempo can be automatically chosen from multiple pieces of music provided by the user. Information about metrics of interest can be provided by signal processing the music during playback, e.g., changing the playback speed, frequency-shifting the music, and emphasizing or deemphasizing particular instruments and voices using signal processing techniques. The timing of active feedback may also be controlled to produce sound at ideal times, e.g., between pieces of music or during quiet intervals.

Control of Other Objects Via Sensing Device

In some configurations, the sensing device detects user gestures and the contraction of particular muscles and, in concert with computation device(s), uses specific actions to enable control of other objects. For example, a user may dance and have the types and intensities of dance steps modify the tempo, instruments, volume, and tones of music, or temporal and color patterns of lighting effects. Examples of actions that may be controlled include sending emails, sending short messages, and controlling building temperature.

Collaboration Use Cases

Multiple sensing and/or interface devices may be used by different uses to enable collaboration, education, and entertainment.

Education and Entertainment Using Real-Time Athletic Activity Metrics

Metrics are numerical values, or vectors of numerical values that are computed based on measurements and/or based on information explicitly provided by individuals. Metrics of interest gathered from one or multiple users can be transmitted to an aggregating computing device for real-time aggregation and display. For example, metrics of interest for users participating in training or competitive sports can be aggregated and displayed, perhaps to large audiences concurrently with live video of the associated athletic activity, for educational or entertainment purposes. These data can also be used off-line, to assist users in emulating other, more advanced, users. For example, a user might emulate the metrics of interest for a group of top athletes in their athletic activity or sport of interest. These data may also be used to assist in judgments in athletic competitions. For example, a sensing and interface device may communicate the time at which a race is started and ended or determine whether sensed data indicate a prohibited action during a sporting event.

Use of Real-Time Data in Mobile Social Networks

Metrics of interest gathered from multiple users by separate sensing devices can be aggregated on computation devices and used to make leaders and participants in the physical activity aware of positions, activities, and physical and emotional states of other participants. For example, individuals involved in group athletic events can use this information to better coordinate their actions toward a shared goal. Another use case is allowing users to compete or collaborate with other users, who might be at physically separate locations. Specific actions may also be used to initiate communication. Action/location/time context may also be used to trigger the interface device to provide information that may be helpful to the user, including information about relevant goods and services.

Real-Time Coaching

During use, data is gathered by the sensor platform and analyzed on the sensor platform, and/or on a remote computing system such as a smartphone, smartwatch, sports watch, and/or on a network-attached server or virtual server. In some embodiments, manual and/or automated coaching (e.g., based on power determinations) is provided to a user (e.g., a runner or walker). Real-time sensing and analysis enables real-time calculation of metrics of interest. These metrics (e.g., the power metric, described in greater detail below) can be selectively provided to users to assist them in reducing or minimizing injury risk, improving athletic performance, and/or improving the benefits of training sessions. Such information can also be used to advise the user on appropriate adjustments in technique to bring about desired results such as improved running and/or walking efficiency, reduced injury risk, improved muscle adaptation results, and/or improved pace. For example, users can be warned when their fatigue levels have reached levels rendering them susceptible to injury. Users who would have better training results by training more or less intensely can be guided to do so by the sensing and interface devices. Users with metrics indicating suboptimal technique can be guided to adjust their technique. For example, runners with excessive braking force can be coached to change their technique, thereby improving athletic performance.

Figure 6:
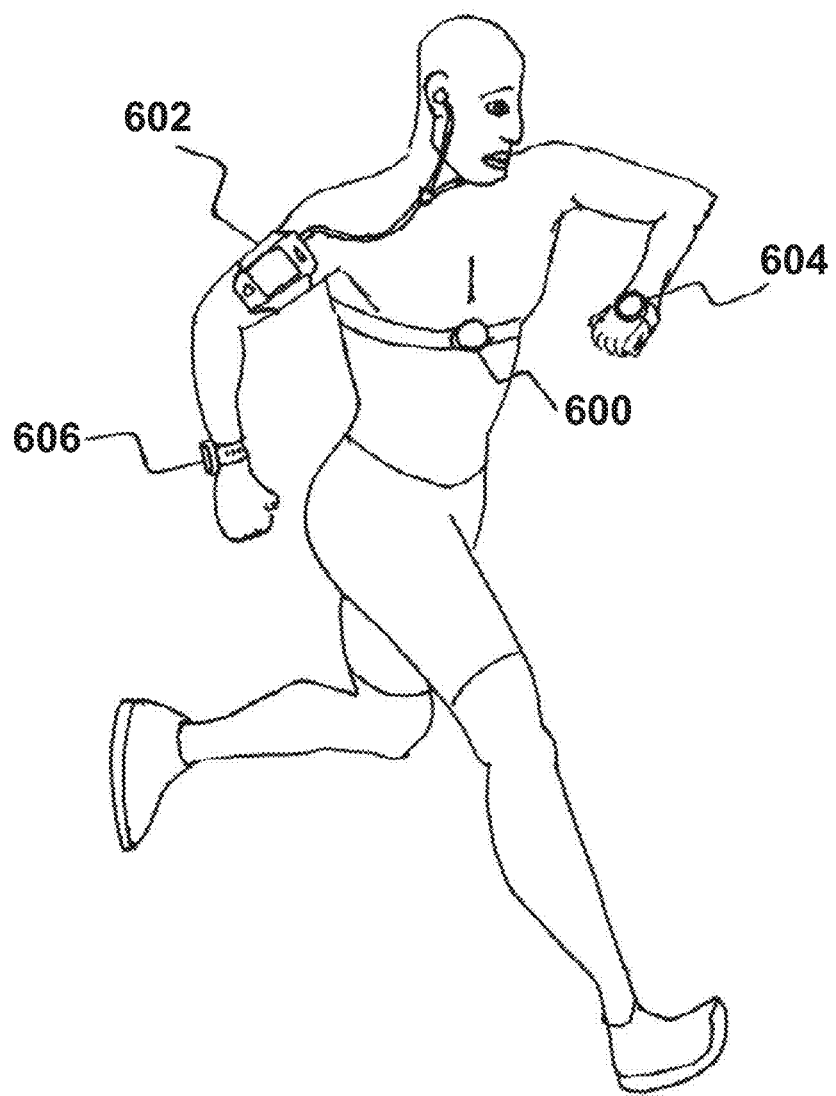
FIG. 6 shows the placement of components of a sensing system on a user, according to some embodiments.

For example, as shown in FIG. 6, a sensing platform 600 can gather and analyze data. The sensing platform 600 may also transmit the data to a remote computing system, such as a smartphone 602, smartwatch 604, sports watch 606, and/or on a network-attached server or virtual server, for analysis. The sensor platform 600 can be used, for example, as part of a sensing system (e.g., as sensor platform 100 in FIG. 1A). The analysis results, including the user's ability to sustain particular power levels for particular durations, can be used to advise the user on appropriate training intensities and durations to bring about the adaptation necessary to reach the user's power and performance goals. Automated coaching can also be used, for example, to warn users of impending overtraining risk and/or to provide advice on pacing. Coaching advice may be provided through vibration and/or sound produced by the sensing platform. Coaching advice may also be provided via vibration, screen display, or audio output from a smartphone 602, smartwatch 604, and/or sports watch 606, e.g., worn or carried by the user. In some embodiments, communication between the sensor platform and other components of the sensing system is carried out through one or more wireless communication technologies such as Bluetooth LE, Bluetooth, Wi-Fi, and Zigbee.

In addition, coaching advice can be provided using comparison's of user running and/or walking techniques with those of expert runners and walkers, and with theoretical ideal techniques based on physiological models of user body structures informed by height, weight, limb, and/or limb segment measurements explicitly provided by the user or inferred based on user motion patterns. The method of displaying user techniques relative to expert or ideal techniques can include display of superimposed comparative animations and/or real-time and offline feedback on specific aspects of technique the user is capable of adjusting, including any of the metrics described herein.

Electrical Power Management

Some components of the sensor platform and/or the sensing system can be shut down periodically to conserve power. In some embodiments, one or more hardware components in the sensing system has its activity state managed in order to achieve the current desired tradeoff between electrical power consumption and measurement accuracy or measurement latency. In some embodiments, the sensors with the highest power consumptions are activated least frequently. Signal processing and prediction techniques can be run by the processor (e.g., residing within the sensor platform and/or within a mobile device in wireless communication with the sensor platform) on data from more power efficient sensors to determine when changes in motion patterns occur that would require activation of more power demanding sensors. In some embodiments, the occurrence of previously encountered patterns in accelerometer data are used to enable estimation of angle changes normally determined using gyroscope and magnetometer data by reusing remembered values instead of re-activating these orientation sensors. The power management states of other portions of the sensing system (e.g., the smartphone 602, smartwatch 604, or sports watch 606 of FIG. 6) are also controlled based on the current accuracy and latency requirements of the sensing system.

Wearable Sensor Platform—Motion Measurements

The mechanical power output of the human body is a function of the velocity and the forces of and on the various parts of the body. In some embodiments, to enable accurate estimation of person and/or limb motion, location, and/or orientation in a compact, low-power package, the activation(s) of an inertial measurement unit (e.g., an accelerometer, such as a three-axis accelerometer), a gyroscope and/or magnetometer, a pressure sensor, and/or a GPS is/are controlled, and their measurements are combined. These components can be integrated within a compact sensing platform (e.g., equipped with a microcontroller) and a wireless communication interface. Computation and sensing can be carried out entirely on a microcontroller in the sensor platform, or some or all computation and/or sensing can be offloaded to a remote device such as a smartphone. The entire sensing system, including the sensor platform and communicating external hardware and software, is herein referred to as the "sensing system."

Depending upon the embodiment, the disclosed sensing system includes one or more of the following capabilities: (1) determine the motion, positions, and orientations of one or more parts of the body of a user wearing the sensor platform, (2) use gathered/sensed data to carry out detailed, and in some embodiments comparative, time-dependent gait analysis of one or more limbs, (3) determine the incline of the user's path, (4) determine the impact of wind on human speed and forces, (5) measure the passage of time, (6) use general physical properties of bipedal motion and a combination of the data described in the above items to determine instantaneous body velocity, force, and the passage of time (thereby allowing power expenditure to be calculated), and (7) control the activities of sensing system components such as sensors (e.g., one or more inertial measurement units, accelerometers, gyroscopes, temperature sensors, inertial sensors, force sensors, pressure sensors, Global Positioning System (GPS) receivers, flex sensors, etc.), processors, wireless communication transceivers, and/or display elements, to reduce or minimize power consumption.

Multiple sensors are capable of providing data allowing person and limb position, motion, and orientation to be estimated. Some of these sensors have higher power consumptions than others when activated. One relatively low power sensor is the inertial measurement unit (IMU, e.g., an accelerometer).

IMU data acquisition: Acceleration samples can be gathered by the IMU (e.g., an accelerometer) at a variable frequency that is adjusted based on the current accuracy and power consumption requirements. These data represent acceleration as viewed from the reference frame of the sensor. However, they may not represent acceleration as viewed form the reference frame of the Earth.

In some instances, IMUs do not allow orientation to be estimated. Therefore, an inertial measurement unit can, in some embodiments, be combined with a magnetometer or gyroscope for orientation estimation. Of these two sensors, magnetometers generally have lower power consumptions.

Reference frame translation: Gyroscope and/or magnetometer samples may be gathered at a variable frequency that is adjusted based on the current acceleration and power consumption requirements. These data may be used to determine the changes in orientation of the sensor relative to the direction of gravity or some part of the user's body. This information may be used, for example, to translate the accelerometer data from its reference fram to the reference frame of the Earth. Some environments, such as indoor environments where large pieces of ferrous metal are present, can interfere with magnetometer use for orientation estimation. In scenarios where magnetometer readings are unreliable, e.g., inconsistent with gyroscope readings, a gyroscope may be used instead.

Over time, measurement error can cause absolute gyroscope orientation readings to accumulate error, thereby producing an absolute orientation that may be inconsistent with reality. In some embodiments, to prevent error accumulation over long time durations, the orientation may be recalibrated with each step. For example, for an embodiment in which the sensing platform is attached to the foot, gyroscope and/or accelerometer readings are used to determine when the foot is placed flat on the ground. The ground angle can be estimated using position and topographical data, or measured using the accelerometer. A proportional integral derivative (PID) algorithm may be used to recalibrate the gyroscope to reduce or minimize the error between the angle measured by the gyroscope and that determined through other means. When the foot leaves the ground, the PID algorithm can be disabled and the gyroscope can be used to measure the angle of the foot until it is again in contact with the ground. The presence of the foot on the ground may be detected by determining when all of the following are true: (1) The downward acceleration is approximately 9.8 m/s$^2$ (note that a different estimation approach may also be used, in which the foot is determined to be on the ground when the length of the vector given by a multi-access accelerometer is approximately 9.8 m/s$^2$); (2) The change in angle over last 50 milliseconds is approximately zero; (3) Foot impact, as detected with an accelerometer, occurred approximately 300 ms prior.

In some embodiments, as a body part (e.g., a limb) rotates, the 3 axis accelerometer reading can be multiplied (e.g., via a processor on board the sensor platform and/or via a remote processor on a mobile device or other device in wireless communication with the sensor platform) by a rotation matrix in order to determine which direction the person is facing.

$$[acc_{x'}, acc_{y'}, acc_{z'}] = \begin{bmatrix} \cos\theta & 0 & \sin\theta \\ 0 & 1 & 0 \\ -\sin\theta & 0 & \cos\theta \end{bmatrix} \times [acc_x, acc_y, acc_z]$$

where $acc_x$, $acc_y$, and $acc_z$ are readings from the three-axis accelerometer, $acc'_x$, $acc'_y$, and $acc'_z$ are the orientation-compensated readings from the three-axis accelerometer, and $\theta$ is the angle measured by the gyroscope. This approach may also be used with the gyroscope being replaced by a magnetometer.

Pressure measurements: A pressure sensor (e.g., an atmospheric pressure sensor, air pressure sensor, barometer, pressure altimeter, and/or the like) can be included in the sensor platform used to detect changes in a user's elevation (i.e., attitude or vertical position). Filtering (e.g., low-pass filtering with a cutoff frequency of ~0.2 Hz, or band-pass filtering with a range of ~0.1 Hz-~0.3 Hz) of the pressure sensor signal can also be used to compensate for air that is incident on the runner (e.g., strong winds, puffs of air, abrupt changes in wind patterns, and/or other aerodynamic factors that cause rapid pressure changes, any of which may vary with time, location, running form, body/limb positioning of the user, and/or other factors) so that the signal is more stable and/or relates primarily to the user's altitude. In some cases where a pressure signal is filtered, the cutoff frequency can be changed dynamically to account for changes in a runner's attitude.

In some cases, the forward motion of a person can be estimated accurately without the use of GPS, and are designed to mitigate or avoid high power consumption and short battery lifespans for the sensing platform. In some embodiments, to avoid frequent activation of a high power consumption gyroscope, a sampling technique is used. A sampling technique in which the gyroscope is deactivated for a subset of paces can result in accumulation of motion and position error for those paces. To reduce or eliminate such errors, an adaptive sampling technique can be used, in which the gyroscope is reactively activated when there is a significant difference between the time-varying multi-axis accelerometer data for that pace and a library of accelerometer data from (not necessarily all) prior paces. When the accelerometer data are similar to those from a prior pace, the gyroscope-enhanced motion estimates from that pace can be used. Accelerometer pace data may be compressed via curve fitting. A subset of paces will have their data stored, with a size limited by available memory and comparison overhead. Heuristics, e.g., based on variation in pace and/or cadence, may be used to make the search for matching prior pace accelerometer data faster.

Although the described position, motion, and orientation estimation technology described is generally quite accurate, some small amount of error can accumulate over long time intervals. Therefore, if a GPS receiver is available, it may be infrequently activated to correct accumulated position estimation error. An inertial measurement unit, magnetometer, gyroscope, and GPS receiver (or subset thereof) can thus be used together, in some embodiments, to accurately estimate person and limb position, motion, and orientation with minimal energy consumption.

In some examples, e.g., to achieve improved accuracy for physiological and/or motion-related measurements, low-frequency measurements can be used to classify activity. For example, a power efficient accelerometer can be used in a low-frequency, low-power sampling mode to classify activity, e.g., walking or running. In some such embodiments, the sensing system can transition to a higher-frequency, higher-power mode, for example when an activity meriting such a transition is detected, e.g., running. In other words, high-frequency measurements can be made when appropriate for the current activity. This transition can be automated, thus requiring no command from, or explicit interaction with, the user. Even in the higher-frequency sampling mode, local data processing can be used to extract relevant and compact features, which can in turn be transmitted to external devices at lower energy cost than the raw measured data. A Fourier transform can be applied to the raw data gathered at low sampling frequency, either on the sensor node or on an external device, allowing temporal features to be detected with high accuracy. Different methods of analysis can also be applied at different sampling frequencies. For example, at low sampling frequency, frequency-domain analysis can be used, and at high sampling frequency, time-domain analysis can be used. This technique facilitates transition among sensing modes with different temporal resolutions and power consumptions without explicit commands or interaction with the user. This achieves a good trade-off between computational/energy cost and feature extraction accuracy.

To estimate change in speed in distance over time with low energy use, contextual information, such as measured stride length for a particular set of physiological and motion-related metrics, can be used together with measurement of motion-related metrics.

Drift compensation: Multiple sensors are capable of providing data allowing person and limb position, motion, and orientation to be estimated. Some of these sensors have higher power consumptions than others when activated. One relatively low power sensor in the inertial measurement unit is typically an accelerometer. However, inertial measurement units typically do not allow orientation to be estimated. Therefore, an inertial measurement unit can, in some embodiments, be combined with a magnetometer or gyroscope for orientation estimation. Of these two sensors, magnetometers generally have lower power consumptions. If feasible for a given implementation, the magnetometer can be used in combination with the accelerometer. However, some environments such as indoor environments where large pieces of ferrous metal are present, can interfere with magnetometer use for orientation estimation. In scenarios where magnetometer readings are unreliable, e.g., inconsistent with gyroscope readings, a gyroscope may be used instead. Although the described position, motion, and orientation estimation technology is generally quite accurate, some small amount of error can accumulate over long time intervals. Therefore, if a GPS receiver is available, it may be infrequently activated to correct accumulated position estimation error. In summary, an inertial measurement unit, magnetometer, gyroscope, and GPS receiver (or subset thereof) can be used together to accurately estimate person and limb position, motion, and orientation with minimal energy consumption.

Techniques described herein allow for the accurate estimation of motion, orientation, and position of a person's limb over time, over both long and short distance scales using a compact device with long battery life. In some embodiments, an IMU, combined with a gyroscope, may be used to determine the orientation of a limb is described first.

In some implementations, human feet are the body parts for which position and orientation are measured. Data collected by the sensor platform may be used to estimate the coarse-grained location of the person. They may also be used to track the paths and orientations of limbs during athletic activities such as running, or swinging a baseball. Orientation-corrected accelerometer readings can be integrated over time (e.g., using a processor disposed within the sensor platform or within a mobile device in wireless communication with the sensor platform) to determine a three-dimensional path of the limbs being monitored by sensing platforms.

In some embodiments, a method of measuring motion of a user during physical activity is performed using a system comprising an inertial measurement unit (IMU) and an orientation sensor disposed within a housing. The method includes: (1) acquiring multi-axis motion data with the IMU at a first sampling rate, where the multi-axis motion represents motion of the housing in a reference frame fixed with respect to the housing; (2) acquiring orientation data with the orientation sensor at a second sampling rate, where the orientation data represents an orientation of the housing with respect to the Earth; and (3) varying the second sampling rate based on the multi-axis motion data. Varying the second sampling rate can include comparing the multi-axis motion data to previously measured multi-axis motion data. Alternatively or in addition, varying the second sampling rate includes estimating when the user is airborne based on the multi-axis motion data, and disabling the orientation sensor when the user is airborne.

An example of a method includes: (1) translating the multi-axis motion data, using the orientation data, from the reference frame fixed with respect to the housing to a reference frame fixed with respect to the Earth so as to yield translated multi-axis motion data; (2) decomposing the translated multi-axis motion data into horizontal motion components and vertical motion components in the reference frame fixed with respect to the Earth; and (3) estimating power expended by the user based on the horizontal motion components and the vertical motion components. The method can include varying the first sampling rate based on a comparison of the multi-axis motion data to previously measured multi-axis motion data. The method can also include measuring changes in pressure experienced by the system due to variations in altitude and/or wind resistance.

Sensing System—Transferring Data to a Mobile Device

A sensing platform as described herein (e.g., sensor platform 100 of FIG. 1A) can be configured to wirelessly communicate with a mobile device (e.g., a smart phone— see 102 of FIG. 1A) via a wireless communications link (e.g., Bluetooth LE, Bluetooth, Wi-Fi, and/or Zigbee) established through a communications port (e.g., communications port 117 of FIG. 1B), for example to transmit sensor data collected during use by a user, to the mobile device for signal processing. In addition, or alternatively, the sensing platform can be configured for wired connection (e.g., communications port 117 of FIG. 1B) with a mobile device (e.g., a smart phone) for the transfer of sensor data collected during use by a user (e.g., stored within a memory disposed within the sensor platform).

Automated Registration and Activation Process

A method and system for activating an electronic device via the Internet is disclosed. In some embodiments, when a user purchases the sensor platform, a server system receives purchaser information, e.g., email address, unique identifier of the sensor platform, etc. After the user/purchaser installs a mobile application on his/her client system (e.g., mobile phone, tablet, smart watch, smart glasses, and/or the like), and during the first-time invocation of the client application (e.g., a mobile software application, or "app"), the server system can transfer the unique identifier of the device to the purchaser's client system, and the sensor platform can automatically be activated and/or connected (e.g., wirelessly) to the purchaser's client system and client application. By way of example, FIG. 7 shows an exemplary automated registration and activation process, according to some embodiments. Automated activation is first enabled (at 701), and a device ID/customer mapping is set (703). The mobile application is then installed (705), after which a server sends a device ID to the client system during the first client application invocation (707).

Sensing System—Data Processing

The processing of raw data/measurements made within the sensor platform can be executed by a processor running on the sensor platform, on a mobile device in communication with the sensor platform (e.g., also functioning as an interface device), and/or on one or more remote servers in communication with the sensor platform and/or the mobile device, to analyze the raw data/measurements (in some embodiments also taking into account contextual information). The sensing system then uses the results to provide advice to users allowing them to adjust their behavior to improve training, competition, and/or recovery results.

Figure 8A:
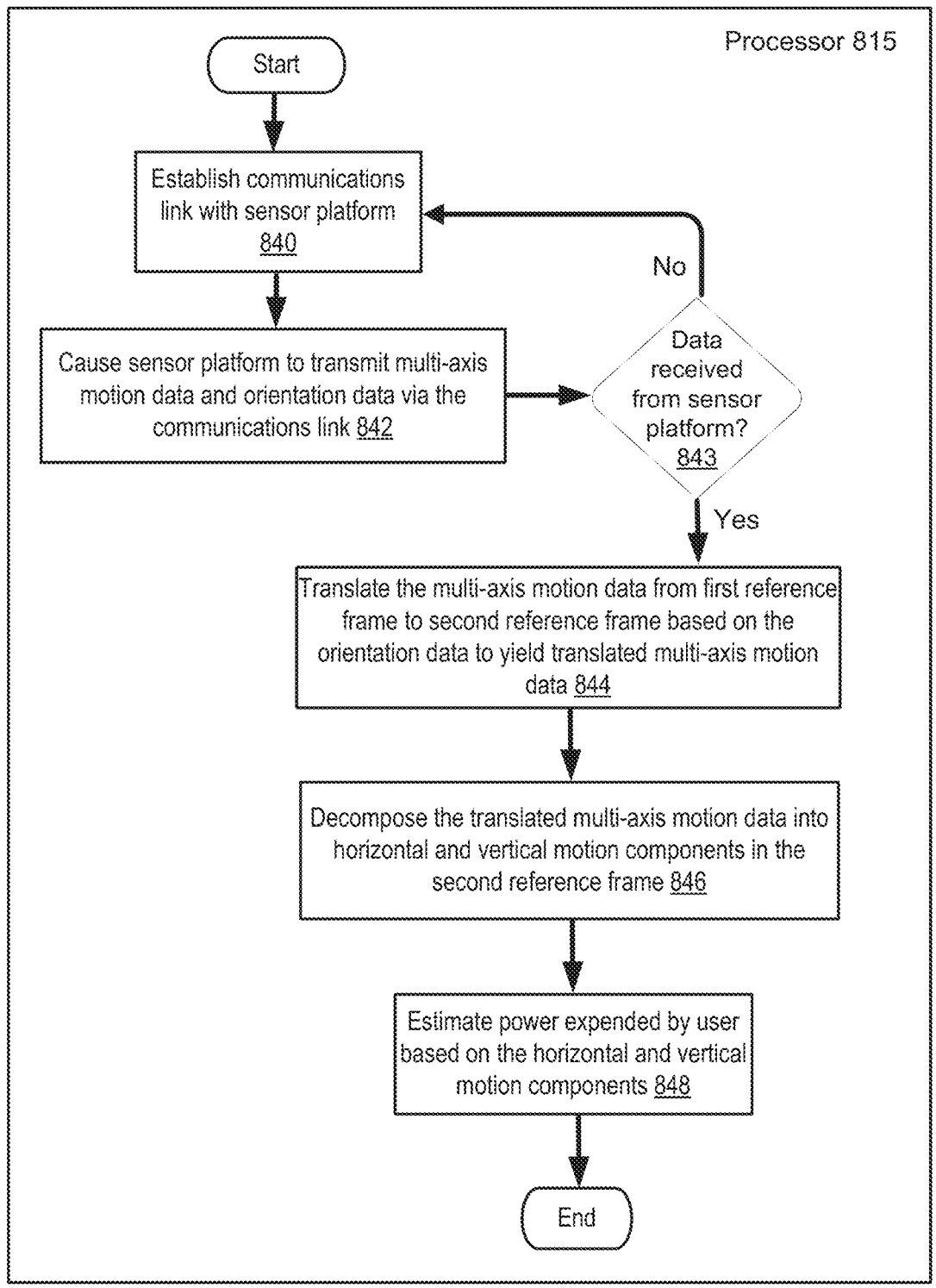
FIG. 8A shows a diagram of the processing of data received by a processor from a sensor platform, according to some embodiments.

An exemplary flowchart, showing the processing of data received from a sensor platform on a processor, is shown in FIG. 8A. A processor 815 (which may be compatible with processor 115 of FIG. 1B, and may reside, for example, in a mobile device) establishes, at 840, a communications link with a sensor platform as described herein (e.g., with reference to FIGS. 1A and 1B). At 842, the processor 815 sends a request to cause the sensor platform to transmit multi-axis motion data and orientation data via the communications link. At 843, if data has not yet been received from the sensor platform (e.g., if the communications link has been interrupted), the processor 815 re-established the communications link at 840. Once the processor 815 has received the multi-axis motion data and orientation data, the processor 815 then translates the multi-axis motion data from a first reference frame (e.g., a fixed reference with respect to the sensor platform) to a second reference frame (e.g., with respect to Earth) based on the orientation data, thereby yielding translated multi-axis motion data. At 846, the processor 815 decomposes the translated multi-axis motion data into horizontal and vertical motion components in the second reference frame. Using the horizontal and vertical motion components determined at 846, the processor 815 then estimates, at 848, the power that has been expended by the user for the period of time in which the multi-axis motion data and orientation data were collected by the sensor platform.

Figure 8B:
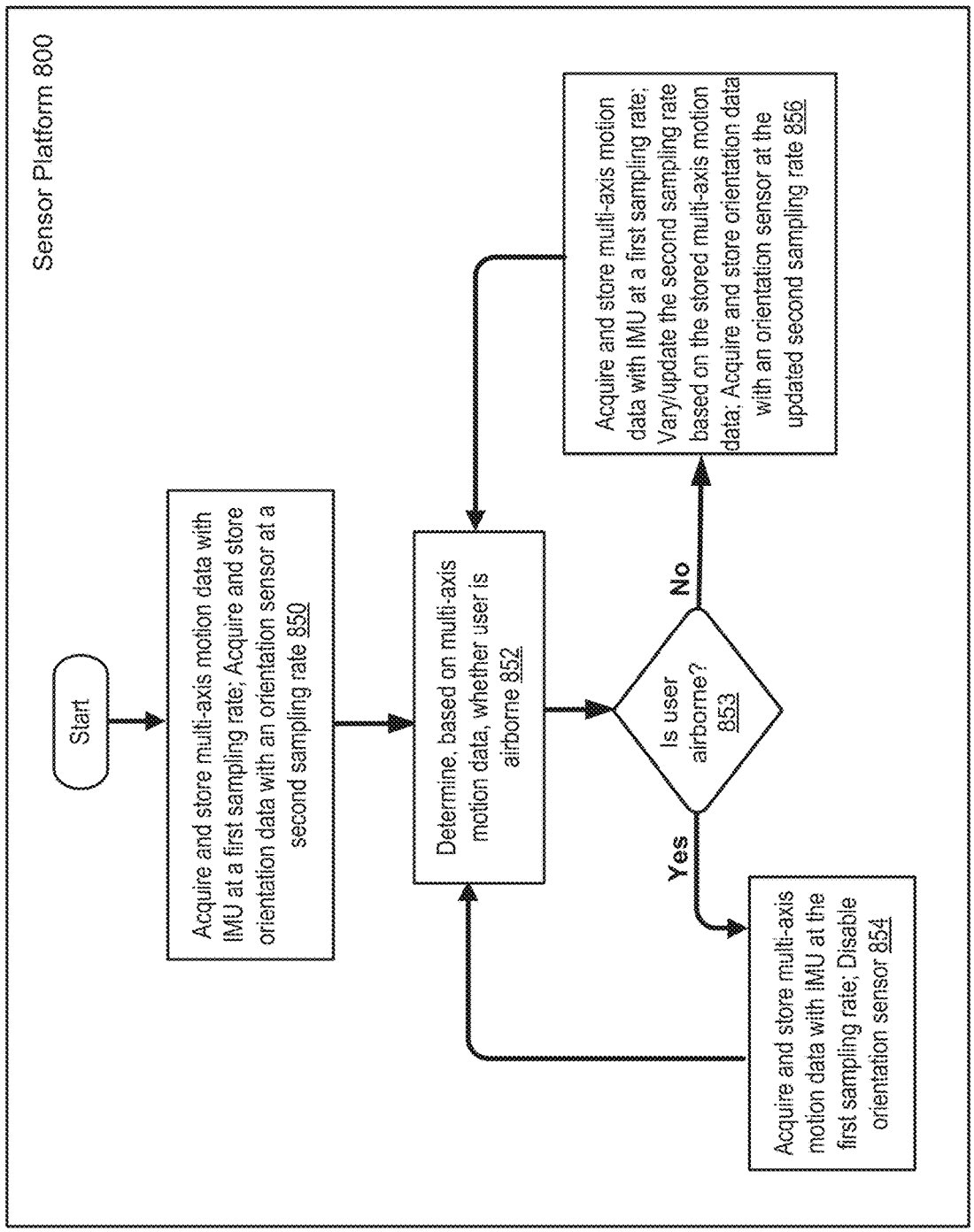
FIG. 8B shows a diagram of the measurement of multi-axis motion and orientation data on a sensor platform, according to some embodiments.

FIG. 8B shows a diagram of the measurement of multi-axis motion and orientation data on a sensor platform, according to some embodiments. At 850, a sensor platform 800 (which may be compatible with the sensor platform 100 of FIG. 1A) acquires, and stores in a memory, multi-axis motion data with an IMU at a first sampling rate, and also acquires, and stores in the memory, (e.g., concurrently) orientation data with an orientation sensor at a second sampling rate. The sensor platform determined, at 852, whether the user wearing the sensor platform 800 is airborne (i.e., his/her feet are not contacting the ground), based on the multi-axis data acquired/stored at 850. If, at 853, the user is airborne, then the sensor platform continues, at 854, to acquire and store multi-axis motion data with the IMU at the first sampling rate, but also disables the orientation sensor. If the user is not airborne at 853, then the sensor platform continues, at 856, to acquire and store multi-axis motion data with the IMU at the first sampling rate, and may vary/update the second sampling rate (of the orientation sensor), e.g., based on the stored multi-axis motion data (which, for example, may be indicative of whether the user is walking, running, etc.). Thus, at 856, the sensor platform 800 also continues to acquire and store orientation data with the orientation sensor, but at the updated second sampling rate. As shown in FIG. 8B, steps 852, 853, 854 and 856 may be iteratively performed, as appropriate, e.g., throughout the duration of time that measurements are taken (e.g., over the course of a run or other bipedal motion of the user).

Figure 9:
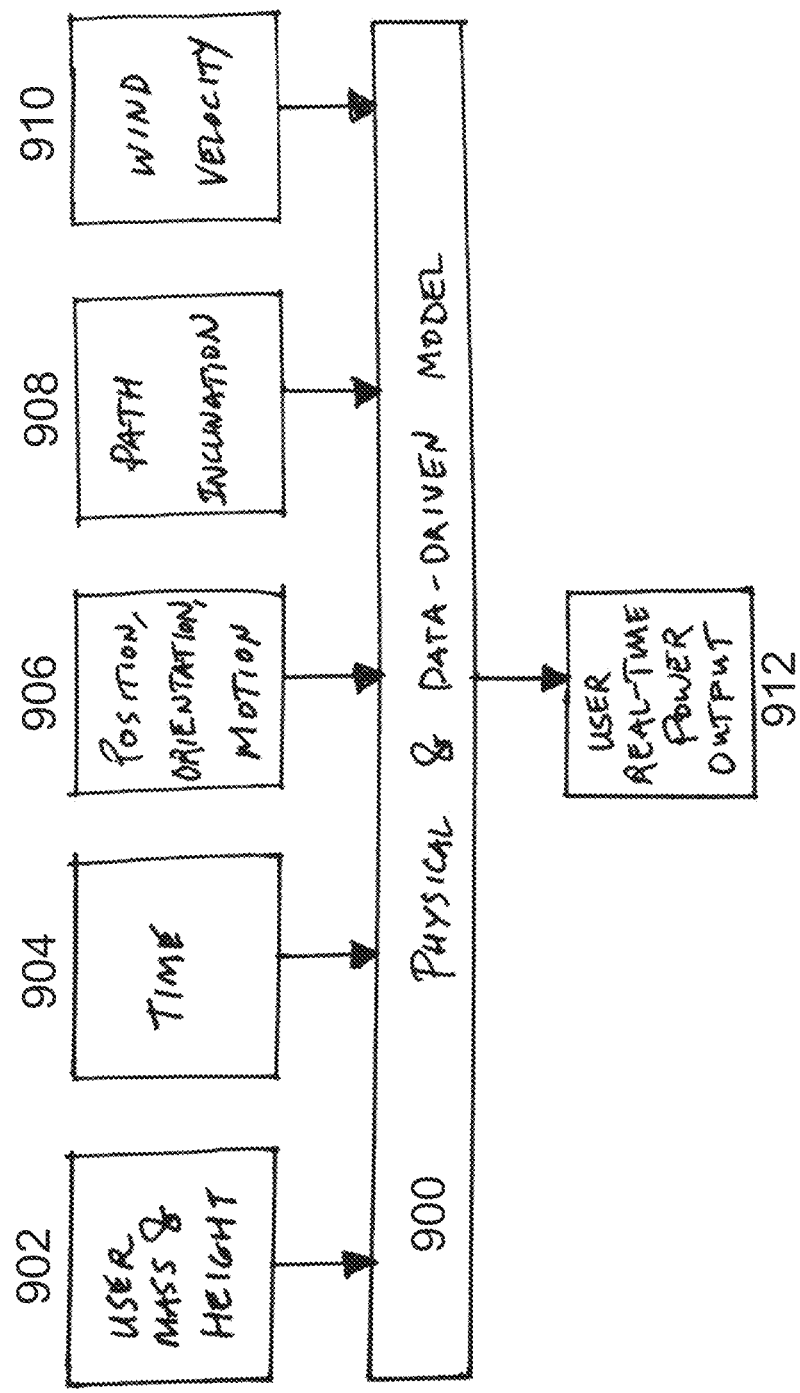
FIG. 9 shows a block diagram of a predictive model, according to some embodiments.

Information derived from sensors and/or from knowledge of constraints on bipedal motion can be supplied to a predictive model (FIG. 9) (e.g., a physical and data-driven model) to estimate accelerations, velocities, positions, and orientations, e.g., based on observed data and/or available knowledge or a subset thereof. For example, as shown in FIG. 9, metrics such as a user's mass and height 902, time 904, position, orientation and motion (906), path inclination 908, and wind velocity 910, are inputs to the predictive model 900, and a user real-time power output 912 is calculated and output.

In some implementations, learned bipedal motion properties for a particular individual are used to increase the accuracy of acceleration, velocity, position, and orientation estimates. These properties may depend on running and/or walking conditions such as incline, fatigue, and pace. Knowledge of running and/or walking conditions can be used to further increase the accuracy of acceleration, velocity, position, and orientation estimates.

The following metrics of interest are calculated based on data gathered from the sensor platform. Their calculation can employ a variety of estimation techniques.

Force Map

The sensor platform may be equipped with one or more location-specific sensors, such as force sensors, flex sensors, and/or temperature sensors, allowing for derivation of a time-varying map of metrics of interest. For example, the device may support measurement of the distribution of impact force across different structures of the feet and legs.

Speed and Distance

Fine-grained limb motion patterns can be used to estimate stride lengths. Timer(s) within the sensing and/or computation devices can be used to determine stride times. These metrics, combined, can be used to calculate the average speed and/or distance traveled of users.

Figure 10:
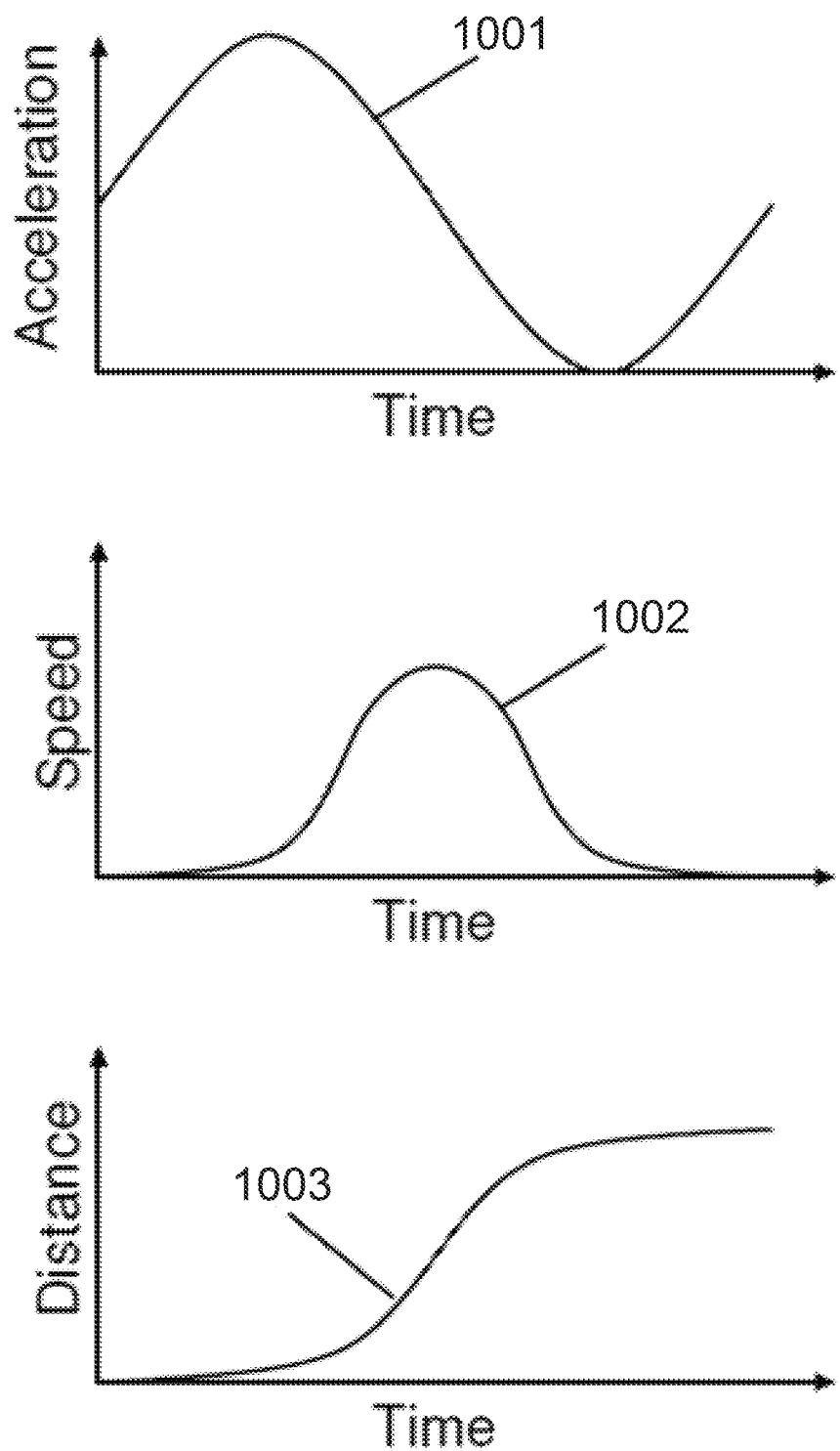
FIG. 10 shows foot acceleration, speed, and distance during bipedal motion, according to some embodiments.

To allow speed and distance to be estimated without frequent use of high energy consumption GPS technologies, data from motion-related sensors calibrated based on context- and person-dependent data can be used. For example, during bipedal motion, foot acceleration can be used to estimate speed and distance. FIG. 10 shows exemplary approximate foot acceleration, speed, and distance for one stride during bipedal motion. In FIG. 10, curve 1001 shows how the foot accelerates with time along the vector pointing in the same direction as the foot, curve 1002 shows how the speed of the foot changes with time along the vector pointing in the same direction as the foot, and curve 1003 shows how the distance of the foot changes with time along the vector pointing in the same direction as the foot. Based on FIG. 10, the distance can be described as follows:

$$\int a e^{-(a-b)^2/c^2} dx = \sqrt{\pi} a |c|,$$

where a, b, and c can be derived by using linear regression to fit a Gaussian distribution to a series of sensor samples or via infrequent calibration to GPS data. By using the learned parameters for a particular individual, and possibly activity, the speed and distance estimation accuracy possible with low-power acceleration sensors is improved.

The accuracy of the speed and distance estimation technique described in the above paragraph can be further improved by infrequent calibration using GPS technology. For example, distance estimation error that may accumulate over long estimation periods can be corrected via very infrequent GPS measurements, thus allowing accuracy typical of GPS with energy consumption typical of acceleration sensors. These infrequent GPS readings can also be used to calculate new calibration parameters for the equations described in the previous paragraph, further improving accuracy even in the absence of future GPS measurements.

Direction

Accelerometers, gyroscopes, and compasses can be used to estimate changes in direction of motion. Contextual information, such as knowledge of motion patterns possible for a particular activity or paths possible from a particular location, can be used to constrain direction estimates, thereby correcting for sensing noise.

Displacement

Techniques described herein, that enable tracking the motion and orientations of body parts over time, may also be used to estimate the coarse-grained location and/or velocity of a person. They may also be used to track the paths and orientations of limbs during athletic activities such as running, or swinging a baseball. Orientation-corrected accelerometer readings can be integrated over time to determine a three-dimensional path of the limbs being monitored by sensing platforms.

In some embodiments, variation in pressure across multiple barometric pressure sensors and time is used to estimate speed and changes in speed.

Incline

Improved estimates of valuable information can be obtained if the incline of the surface on which the user is moving is known. To determine current incline, the instantaneous derivative of altitude can be approximated by combining timed barometric pressure samples and pace data to allow fitting of a linear incline function, for example to determine instantaneous incline, thereby making long-term variation in barometric pressure due to changes in weather irrelevant. Alternatively or in addition, incline can be estimated using the position and direction estimation techniques described herein and a map stored on the sensing system translating from position and direction to incline. Incline can also be determined by pressure measurements (using a pressure sensor, such as a barometer, pressure altimeter, and/or the like). For example, a pressure sensor can be used to detect changes in a user's elevation (i.e., attitude or vertical position). Low-pass filtering (e.g., with a cutoff frequency of ~0.2 Hz) of the pressure sensor signal can also be used to compensate for air that is incident on the runner (e.g., strong winds, abrupt changes in wind patterns, and/or other aerodynamic factors). The cutoff frequency can be changed dynamically to account for changes in a runner's attitude.

Body Forces

One or more of the following data elements can be used to estimate the forces acting on particular body parts, including the center of mass: acceleration data in body or Earth frame of reference, incline, user weight or mass, and user height. Mass and height may be used to estimate the distribution of body mass across different parts of the body.

Force can be calculated using knowledge of change in kinetic energy over time, $m \times a$, where m is mass and a is the acceleration. In one embodiment, force acting on a runner's center of mass is estimated using the acceleration at the sensing platform location. By knowing the weight and height of the person, a scaling factor can be used to scale the acceleration seen at a sensor location, such as the hip or trunk, to the acceleration of the center of mass across a wide range of running speeds and cadences. A general scaling factor may be used for all users, or a user-specific scaling factor may be used if more information about the user's body structure is known. These approaches can be used to estimate both vertical and horizontal forces.

The inventors have determined, through laboratory testing, that when running downhill, only a portion of potential energy is recovered and can be used to permit reduced muscle power for the same overall force acting on the body center of mass. Therefore, a potential energy recovery efficiency scaling factor can be used to determine the impact of up-hill or down-hill running on body output power. In other embodiments, instead of using a scaling factor, the velocity of the body part of interest is again integrated to determine the position and the following expression is used to estimate the power required for vertical motion:

$$\frac{kmg\Delta h}{\Delta t},$$

where k is a scaling factor, m is the mass, g is the acceleration due to gravity, $\Delta h$ is the change in sensor height, and $\Delta t$ is the change in time.

Wind Effect

Wind may affect human velocity and required force exertion, and hence the mechanical power output. The sensing platform may determine the wind effect and the corresponding impact on power using one or more of the following methods:

The IMU reports the real-time linear and angular acceleration. Using a method described herein, the linear acceleration along the physical dimension can be determined. When the human is running, the forward acceleration a can be determined during the air time, i.e., when the human body is completely left the ground. Then, the wind-induced force can be determined as $m \times a$, where m is the body mass. Next, the wind-induced power can be determined by $v \times f$, where v is the body velocity along the forward direction.

The pressure sensor(s) (e.g., barometric sensor(s)) can also be used to determine the wind-induced power. In some embodiments, the air pressures at the anterior and posterior of the user's body are measured by the sensing platform, and the difference between these two, i.e., wind pressure P, is computed. Then the wind-induced force can be determined by $A \times P \times C$, where A is the body forward-facing surface area, and C is the drag coefficient.

The wind effect can also be estimated as follows. First, human body velocity information is estimated using inertial sensors and/or GPS sensors. The wind velocity is determined using an in-situ wind sensor or third-party weather information. Then, the relative velocity, v, between the human body and wind can be determined. Next, the wind pressure can be determined by $K \times v^2$, where K is a coefficient.

Impact

Temporal changes and patterns in the acceleration experienced by the sensing device can be used to determine the time of impact, after which samples in a short time window can be used to estimate impact forces along multiple physical axes.

Ground Time and Air Time

Full frequency spectrum motion metrics can be analyzed to determine when a user's limb is in contact with the ground, allowing calculation of ground time and air time. These metrics can be used to guide users toward improvement in athletic form.

User Power Capabilities

In some implementations, the sensing system automatically characterizes the physical condition of its user, with or without active changes by the user. Simply wearing the sensing platform during training and/or competition allows data to be gathered on the durations that particular power outputs are sustained by the user's body. These data can concurrently and/or subsequently be used to automatically determine the power outputs at which transitions between different operating zones, such as aerobic and anerobic, occur. Users can also be provided with a plan that indicates target power levels during training, allowing more rapid characterization.

The force and position change information determined as described herein, combined with measurements of elapsed time, can be used to estimate the power expended to move a part of the user's body. In one embodiment, the power exerted to move the body center of mass is determined. In addition to, or as an alternative to, center-of-mass power estimation, power applied to individual body parts can be estimated. For example, using power applied to legs for step-by-step acceleration and deceleration in addition to center-of-mass power permits a more accurate estimate of whole-body power expenditure. An average human, or specific user, power generation efficiency function may be used to translate whole-body power expenditure into metabolic energy expenditure.

A user's ability to sustain specific power outputs for specific durations may also be used to estimate the composition of activity-relevant muscle groups. In one embodiment, the percentage of fast-twitch and slow-twitch muscle fibers in the muscles used to generate most power during running can be estimated by measuring the position and slope of a plot of duration as a function of power output when running.

Power Number

One embodiment of the present disclosure determines the power being exerted by a human body's muscles on itself using dynamically changing data gathered using a compact body-mounted wireless sensing platform containing one or more of the following sensor types: three-axis accelerometers, gyroscopes, magnetometers, Global Positioning System (GPS) receivers, and atmospheric or air pressure sensors. This power measurement may be used to assist athletic training.

The sensing system can incorporate implementations of signal processing techniques that take into account known physical properties of human running and/or walking behavior to determine forces and/or velocities. Combined with an in-system timer, the force and velocity information permit the calculation of body power consumption (e.g., a "power number"). The power number can also be derived, at elast in part, from acceleration measurements (e.g., collected by the IMU of the sensor platform).

This power number can be used, e.g., in combination with pace and/or duration, to guide the user toward more appropriate training, pace, and running and/or walking technique. For example, power can be used to enable users to understand the relationship between body power output during running and/or walking and the durations particular power outputs can be maintained. This relationship can be used to quantify the strengths and weaknesses of users, and suggest changes in training plans. Body power output can also be used during runs to recommend appropriate instantaneous paces to users in order to increase or maximize entire-run pace in the presence of varying fatigue and running and/or walking environment. Power is also used to determine which changes in running and/or walking form or technique improve or degrade running and/or walking efficiency. Running and/or walking efficiency at a particular speed is inversely related to running and/or walking power.

Efficiency

Metrics of interest associated with energy use that is not useful or less efficient, e.g., vertical motion when the goal is horizontal motion, etc., are used to estimate efficiency, i.e., energy productively used divided by total energy used. For example, cadence, fine-grained three-dimensional limb motion patterns, and impact forces may be used to estimate running efficiency.

Drift-Cancellation for Indoor Location Tracking

Some metric estimation techniques, such as speed, distance, direction, and temperature estimation, may result in an accumulation of errors over time. This can, for example, be a result of time-integration of sensor readings such as accelerometer readings. To compensate for this drift error, temporal and environmental cues can be used. For example, certain repetitive activities such as walking can periodically expose the sensing device to a known velocity, e.g., zero velocity relative to ground when the foot is in contact with the ground. By detecting actions that imply particular metric values, the drifted estimates are calibrated to the actual action-implied values. The same concept is applied to location tracking when there are occasionally available accurate location estimates, such as GPS or wireless environment readings. Environmental invariants, such as impossibility of traveling through walls, can also be used to calibrate location and direction estimates.

Pacing

The user power output capabilities described herein can be used to determine the optimal pacing schedule during a run to reduce or minimize the time to complete the run. In some implementations, for each stage of a run, the power output to pace relationship is largely dependent on running and/or walking path incline. Given knowledge of a planned running and/or walking path, the path can be divided into segments. Each segment can have/be assigned an incline- and/or wind-dependent equation relating power to pace. Duration for the segment can therefore be determined as a function of power. Reducing or minimizing the total duration of the run by dynamically adjusting power output can be achieved by setting segment power output values under constraints on the maximum duration sustainable for each power output level. In other words, a goal of reducing or minimizing run duration can be formulated as a constrained convex optimization problem and solved, with gradient descent or conjugate gradient search being used in the preferred embodiment.

If the planned running and/or walking path is not known, future incline angle can be estimated based on average incline angle for the portion of the run already completed. If it is specified by the user that the running and/or walking path is a cycle, then the average incline angle for the portion of the run already completed can be negated to estimate the remaining incline angle. In some embodiments, the pacing technique is otherwise identical to that described elsewhere herein.

Metrics calculated from foot and body motion and orientation paths can also be used to characterize user running and/or walking techniques. Such metrics include, by way of non-limiting example, air time, ground time, cadence, stride length, foot-to-ground angle at impact, fibula-to-ground angle at impact, rate of loading upon impact, and maximum vertical body displacement during stride. For each metric, the difference between left and right stride is determined, which is used to assess asymmetry.

Activity Detection

The sensing device and metric estimation techniques described herein can be used to determine time-, location-, and user-dependent activities. For example, periodic fine-grained limb motion paths can be used to determine whether a user is walking, running, playing basketball, or dancing. Specific moves within activities can also be detected. For example, dance steps such as toe, ball heel, toe stand, the basic movement for any particular dance, chasse, heel turn, or any other particular steps associated with dance can be detected. Similarly, moves in martial arts or yoga forms can be detected. Signal processing and machine learning techniques can be used, for example, to detect actions of interest in any physical activity in which motion or muscle contraction patterns are repeated. The technique may be calibrated to person-by-person variations in moves.

Characterizing User Technique

In some implementations, the running and/or walking techniques of users are characterized by measuring their 3-D foot and/or body motion and rotation paths. These paths are used to compare a user's technique with those of expert athletes and/or theoretically ideal paths. These paths, including the sagittal foot path, can be used to illustrate to users how their techniques differ from preferred techniques.

Emotional and Physical State Detection

The emotional states of users influence many of the metrics computed based on measurements made by the sensing device. Values, temporal patterns, and spatial patterns in these metrics can be used to estimate the emotional and physical states of users in order to provide advice or encouragement, or to change the manner in which information is provided to be better suited to the user's current emotional and physical states. For example, tired individuals may have peculiar fine-grained motion patterns, allowing automatic adjustment in exercise recommendations. Similar changes in motion patterns may be used to detect depression.

If change is constantly or too frequently advised by the sensing system (e.g., changes proposed to the user), the user may be distracted and have a poor experience. Instead, the distributions of multiple motion-related and physiological metrics such as impact intensity, ground time, air time, step rate, vertical motion, impact position, the positions of limbs and body, heart rate, skin resistance, and muscle contraction intensity can be calculated to characterize the user's current state. These distributions can be used to inform the advice provided to the user. For example, if a user is having a difficult training day, on which step rate has a high variance and is very frequently outside the optimal range, the user can be advised to modify his behavior only occasionally to prevent/reduce annoyance and cognitive overload. Knowledge of metric distributions such as that of step rate can be used to ensure that users are prompted to modify their behavior when their metrics deviate by the largest amount from the ideal range. In other words, the thresholds used to provide prompting to the user can be dynamically adjusted based on the user's capabilities at the time, as measured though the distributions of multiple motion-related and physiological metrics.

Mapping

The direction and position estimation techniques described herein can be used to provide position and route data to support automatic derivation of maps of passable interior and exterior routes as well as regions in which people congregate. These maps can be automatically labeled with relevant information about the implications for bipedal motion, e.g., the energy use for regions of a particular hiking trail can be incorporated in the map, as can the influence on ground material in particular indoor and outdoor locations. Locations may also be labeled based on the activities and emotional states of people who have previously occupied the locations.

Detection of Asymmetry

Metrics of interest, as well as unprocessed sensed values, can be used to detect asymmetries in motion, e.g., differences in the intensities, speeds, or motion patterns of right and left limbs. This information can be used to detect evidence of unbalanced development or injuries, and this evidence can be used to automatically or manually make recommendations of changes to technique, training methods, and training intensities. Inefficiencies resulting from asymmetries in antagonistic muscles and nerves can be identified in this manner.

Fatigue Estimation and Use

To detect the effects fatigue on muscles, nerves, and other tissue distributed throughout the body, the sensing system may gather physiological and motion-related data, and computationally convert these data to metrics. When muscles and other tissues become fatigued during physical activity, the shapes of the distributions of related metrics can also change. The sensing system may include one or more modules. Changes (e.g., dynamic changes) to the power and form metrics described herein can be used to identify/determine the fatigue state of the user. For example, dynamic increases in the variance and mean of the step rate distribution can be used to identify fatigue. The time-varying changes in one or more parameters (including mean, variance, and kurtosis) of the distributions of one or more metrics (including impact intensity, ground time, air time, step rate, vertical motion, impact position, the positions of limbs and body, heart rate, skin resistance, and muscle contraction intensity) can be used to detect fatigue. Other motion features, such as ankle dorsiflexion/plantarflexion angular velocity, hip flexion, and hip/knee extension, can also be used to assist fatigue detection. For example, increase in step rate variance and decrease in step rate mean can be used to detect fatigue. In some embodiments, a default set of threshold-exceeding changes, including a decrease in power output after compensating for incline, a change in cadence, a chance in stride length, or in any of the form metrics, are used to identify the onset of fatigue.

The metrics and change thresholds used to identify fatigue can be automatically calibrated and/or adapted to individual users based on changes observed when the user enters detectable fatigue states, and/or based on explicit reports by the user via the sensor platform, smartphone, smartwatch, and/or sports watch. The sensor platform may also be equipped with heart rate measurement capability. Then, fatigue can also be determined by comparison between power and heart rate. Specifically, if the measured power begins to decrease but the heart rate begins to increase, it can indicate that the user is at the onset of fatigue. In some embodiments, the event of the variance in measured power over some time period exceeding a threshold value may be used to detect fatigue, or the variance itself may be used as a continuous measure of fatigue (see, e.g., FIG. 10, discussed further below).

Critical Power Estimation and Use

Figure 11:
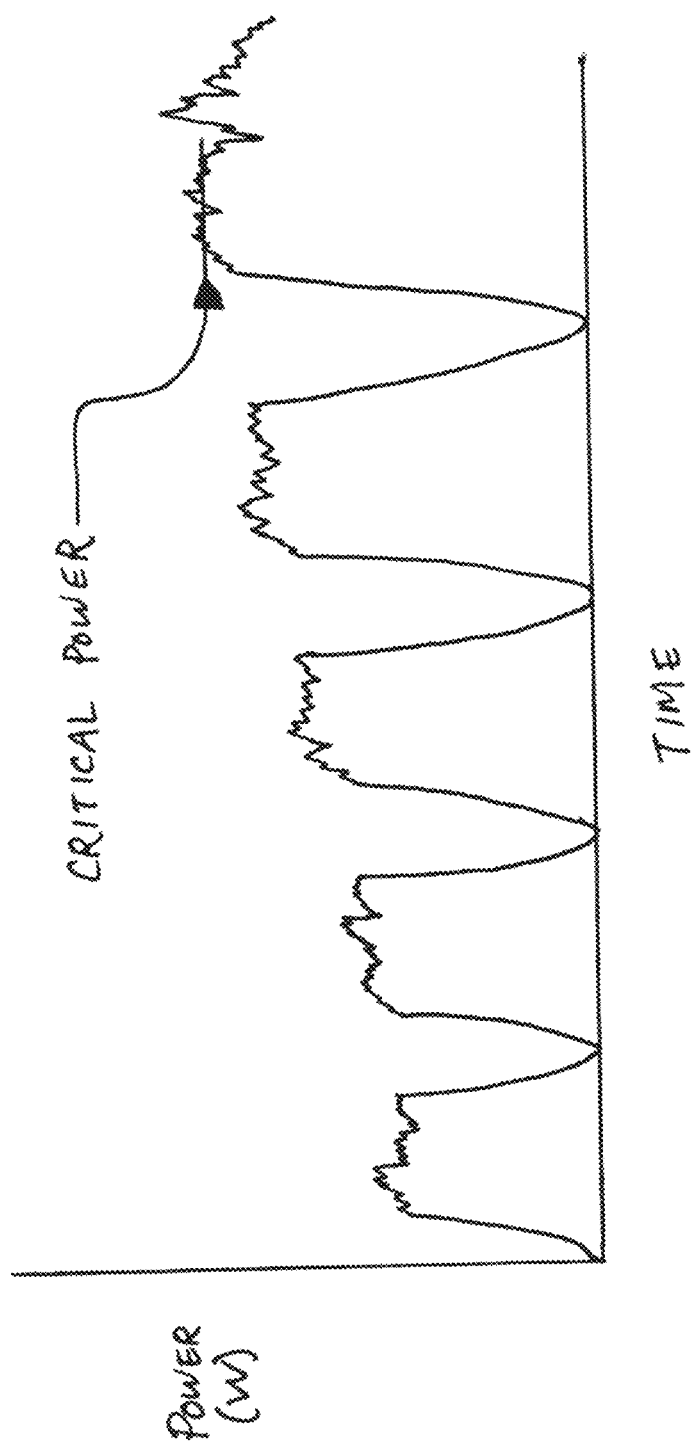
FIG. 11 shows a plot of power variation over time, according to some embodiments.

FIG. 11 shows a plot of power variation over time for a user, including an indication of critical power, according to some embodiments. Critical power is defined as the maximum power that a user can achieve for a relatively long or sustained period of time, which can be used to develop sports training plan. For example, in some embodiments, given the critical power measure p, the training intensity of individual training zones and/or levels, e.g., recovery, fat burning, tempo training, and interval training, can be determined by K×p, where K is a training zone and/or level-specific scaling factor. To measure critical power, the user may follow a specific testing protocol, with power being measured by the Sensing Platform. Or, the sensing platform can also automatically determine critical power by measurement during day-to-day use. Using running as an example, a runner can follow a testing protocol, including but not limited to, 3-min and 10-min max-effort test, 30 minute max effort test, 2-mile max effort test, and 4 times 5-min all out test. After the critical power is determined, the corresponding training zones and/or levels can be determined accordingly. The user can follow the training plan and use the sensing platform to monitor and guide training intensity.

Fitness Assessment

The sensor platform can assess the user's fitness level using power measurement. Consistently improved capability to produce higher levels of power, and/or sustain them for longer periods of time, indicates the improvement of the user's fitness level. In some embodiments, the sensing platform is also be equipped with heart rate measurement capability. In such embodiments, the power-heart rate ratio can also be used to assess the user's fitness level. Specifically, if the ratio increases, due to increase of power and/or decrease of heart rate, it indicates the user's fitness level improves. On the other hand, if the ratio decreases, it indicates the user's fitness level degrades and/or the user begins to experience fatigue.

Additional Metrics

In addition to the metrics described above, the system may calculate the following metrics, which are used to provide feedback to users of the system. The functions on which the following metrics depend are described herein (e.g., below). These metrics can be used to compare different time intervals or different individuals.

The inputs used when computing the following metrics can include time-series vectors with equal lengths, such as: GroundTime, AirTime, PaceMinPerMile. Regions of interest in the above vectors can be selected using the StartIndex and StopIndex variables. For example, to select an entire time series, StartIndex is set to 1 and StopIndex is set to the length of the vector. To use a quarter of a time series, StartIndex is set to 1 and StopIndex is set to one fourth the length of the vector.

1. Efficiency: This metric can be used to determine how much of the energy expended in bipedal motion is used productively to produce or maintain forward motion. It is calculated as follows.

$$\text{Efficiency}=\text{Normalize}(\text{Mean}(\text{StartIndex},\text{StopIndex},1/(\text{AirTime}*\text{PaceMinPerMile}/1000))),$$

where AirTime is the amount of time in milliseconds per stride during which the foot of the person being monitored is not in contact with the ground and PaceMinPerMile is the pace in minutes per mile of the person being monitored. Efficiency can be calculated for various time ranges, as specified by the StartIndex and StopIndex variables.

2. Fatigue: This metric can be used to indicate how fatigued a person is. It is calculated as follows.

$$\text{Fatigue}=\text{Normalize}(\text{Mean}(\text{StartIndex},\text{StopIndex},\text{Clean1}(\text{GroundTime}/\text{AirTime}))),$$

where GroundTime is the amount of time in milliseconds per stride during which the foot of the person being monitored is in contact with the ground.

3. Consistency: This metric can be used to indicate how consistent the running form of the individual being monitored is. It is calculated as follows.

$$\text{Consistency}=\text{Normalize}(\text{StdDev}(\text{StartIndex},\text{StopIndex},\text{Clean2}(\text{AirTime}/\text{GroundTime}))).$$

4. Performance: This metric can be used to indicate a speed-independent measure of body performance. It is calculated as follows.

$$\text{Performance}=\text{Normalize}(\text{Mean}(\text{StartIndex},\text{StopIndex},\text{Clean2}(\text{AirTime}/\text{GroundTime}))).$$

5. Quality: This metric can be used to indicate the overall quality of running. It is a function of the other metrics described in this section.

$$\text{Quality}=\text{Normalize}(\text{Efficiency}-\text{Fatigue}+\text{Consistency}+\text{Performance})$$

Calculation of the above metrics may be modified to produce absolute instead of relative values by omitting the normalization stage. Note that these metrics may have immediate impact on the behavior of the individual being monitored in a way that would be impossible were they calculated mentally. The metrics, when used, are used within a system that can provide immediate feedback to its users, thereby allowing adjustment of running form, exertion, or other aspects of their running.

The following functions can be used, in some embodiments, to support calculation of the metrics described above.

$$\text{Clean 1( )}=\text{FunctionOutput}=\text{"if FunctionInput}>=\text{Threshold1, include input in the output set"} \qquad 1.$$

This function removes beginning & ending outliers, and data points associated with walking. Threshold1 may be adjusted depending on the data set. By way of example, a value of 0.35 has been found to work well in practice.

$$\text{Clean2( )}=\text{FunctionOutput}=\text{"if FunctionInput}<\text{Threshold2, include input in the output set"} \qquad 2.$$

This function removes beginning & ending outliers, and data points associated with walking. Threshold2 may be adjusted depending on the data set. By way of example, a value of 3 has been found to work well in practice.

$$\text{Normalize( )}=\text{FunctionOutput}=(((\text{MaxDVal}-\text{MinDVal})*(\text{FunctionInput}-\text{MinVal}))/(\text{MaxVal}-\text{MinVal}))+\text{MinDVal}, \qquad 3.$$

where MaxDVal and MinDVal are the maximum and minimum desired values, respectively, and MaxVal and MinVal are the maximum and minimum values in the data set of interest, which may contain data from different time intervals and different individuals.

For any of the calculations described herein, additional constants/terms can be included to compensate for noise, variation between individual users, changes in device position on the user, etc. The additional constants/terms can include lower-order velocity components, constants based on studies of many users (e.g., runners), constants based on measurements for a specific user, etc.

A method of estimating power expended by a user while wearing a sensor platform containing an inertial measurement unit (IMU) and a memory can include storing, in the memory, (i) multi-axis motion data and (ii) orientation data, where the multi-axis motion data represents motion measured by the IMU in a first reference frame fixed with respect to the sensor platform, and the orientation measurements represent orientation of the sensor platform in a second reference frame fixed with respect to the Earth. A communications link is established between a processor (e.g., of a mobile device) and the sensor platform. The sensor platform is caused to transmit the multi-axis motion data and the orientation data to the processor via the communications link. The processor translates the multi-axis motion data from the first reference frame to the second reference frame based on the orientation data so as to yield translated multi-axis motion data. The processor decomposes the translated multi-axis motion data into horizontal motion components and vertical motion components in the second reference frame. The processor then estimates the power expended by the user based on the horizontal motion components and the vertical motion components (for example, vertical power expended may be estimated based on the vertical motion components and horizontal power expended may be estimated based on the horizontal motion component).

Vertical power can be estimated as follows:

$$Power_{vertical} = \frac{k1 \times m \times g \times \Delta h}{\Delta t}$$

where k1 is a scaling factor, m is the mass, g is the acceleration due to gravity, $\Delta h$ is the change in height, and $\Delta t$ is the change in time. $\Delta h$ can be understood to be an "incline of a path" of the user (e.g., a runner), and can be determined by pressure sensor readings (e.g., barometer 101 of FIG. 1B, or by any other atmospheric or air pressure sensor), vertical motion data acquired from the IMU (e.g., a three-axis accelerometer), and/or GPS-derived position data. In some implementations, to save on battery power consumption, GPS position data is not acquired, or is only infrequently acquired (e.g., to recalibrate measurements, etc.).

Horizontal power can be estimated as follows:

$$Power_{horizontal} = k2 \times F \times V = k2 \times m \times a \times V$$

where k2 is a scaling factor, F is the force, m is the mass, a is the acceleration, and V is the speed.

In addition, or alternatively, horizontal power can be estimated as follows:

$$Power_{horizontal} = \frac{k3 \times m \times V \times \Delta V}{\Delta t} \approx \frac{k4}{\Delta t} \times (k5 + k6 \times \Delta V) \times \Delta V$$

where k3, k4, k5, k6 are scaling factors, m is the mass, a is the acceleration, and $\Delta V$ is the change of speed during the period of $\Delta t$.

The scaling factors (k1, k2, k3, k4, k5, k6) may be empirically determined based on measurement of one or multiple users (e.g., averaged across a group of runners and thus broadly applicable) and/or determined based on information provided by the specific user (e.g., the scaling factors can be "constants" that are computed for an individual user based on measured, tested, historical, and/or known parameters/values). "Known" parameters/values can refer to parameters/values that have been manually entered into the sensing system (e.g., via a user interface) by the user or a trainer. Each of the scaling factors (k1, k2, k3, k4, k5, k6) can be human-specific, user-specific (e.g., based on their level of general physical fitness, sport-specific fitness, running form, height and/or weight, muscle conditioning, genetics, etc.), body part specific, and/or specific to a given environment, terrain, elevation, types of apparel or footwear that a user is wearing, etc. In some implementations, one or more of the scaling factors or constants may be initialized to have generalized values (e.g., based on studies of a large group of individuals) and, over time, as the sensing system has gathered, stored, and/or processed sensor data for a specific user, the scaling factors or constants may vary to become more customized, either automatically or by manual request of a user.

In some cases, one or both of the above estimates of power expended by the user accounts for the wind resistance (e.g., based on pressure sensor data), e.g., via one or more of scaling factors (k1, k2, k3, k4, k5, k6) and/or.

Estimating the power expended by the user can include estimating power expended for vertical motion of the user. Alternatively or in addition, estimating the power expended by the user can include scaling, via a scaling factor, an acceleration of the user to the user's center of mass, for example, wherein the scaling factor is based on a height of the user and a weight of the user.

The method can include estimating a metabolic energy expenditure (i.e., calories burned) of the user based on the power expended by the user. The metabolic energy expenditure can be estimated as follows:

$$Energy_{metabolic} = \int_{T1}^{T2} \frac{Power(t) \times (1 - k7(t))}{l(t)} dt$$

where Power(t) is the power output at time t, k7(t) is a coefficient which measures the contribution of recycled power during human running, l(t) is the running economy coefficient, which measures the percentage of the metabolic energy transformed into mechanical power output. T1 and T2 define the period of time of interest.

The metabolic energy expenditure can also be estimated as follows:

$$Energy_{metabolic} = \int_{T1}^{T2} Power(t) \times Constant(t) \, dt$$

where Power(t) is the power output at time t, T1 and T2 define the period of time of interest, and Constant(t) is an empirically-determined and/or customized constant value based on or derived from one or more of the following: (1) k7(t) (the coefficient which measures the contribution of recycled power during human running); (2) l(t) (the running economy coefficient, which measures the percentage of the metabolic energy transformed into mechanical power output); (3) measured or known lactate threshold or anaerobic threshold of the user; (4) measured, historical or known $VO_2$ max (maximal oxygen consumption) of the user; (5) measured, historical or known running economy of the user; (6) measured, historical or known performance-impacting physiological parameters of the user; and (7) measured, historical or known performance-impacting physiological parameters of a "typical" or "average" runner (e.g., as determined by averaging across a general pool of runners, or as determined by averaging across a pool of runners that matching a specified profile of the specific user). "Known" values can refer to values that have been manually entered into the sensing system (e.g., via a user interface) by the user or a trainer.

The sensor platform can include a pressure sensor, and the method in such instances can include: (1) causing the sensor platform to transmit pressure data to the processor via the communications link, the pressure data representing pressure measurements by the pressure sensor; and (2) estimating, by the processor, wind resistance experienced by the user based on the pressure data. Estimating the power expended by the user can include accounting for the wind resistance. In other instances where the sensor platform includes a pressure sensor, the method can include: (1) causing the sensor platform to transmit pressure data to the processor via the communications link, the pressure data representing pressure measurements by the pressure sensor; and (2) estimating, by the processor, an incline of a path of the user based on the pressure measurements and the translated multi-axis motion data.

The method can include estimating (e.g., via a processor running on the sensor platform and/or on a mobile device in wireless or wired communication with the sensor platform) one or more of a plurality of metrics of interest. For example, a stride distance of the user can be estimated based on the multi-axis motion data and/or the translated multi-axis motion data as described herein. An amount of time during a stride of the user that a foot of the user is airborne can be estimated based on the multi-axis motion data and/or the translated multi-axis motion data. An efficiency of the user can be estimated based on the power expended by the user and the an amount of time during the stride of the user that the foot of the user is airborne. An amount of time during the stride of the user that the foot of the user is in contact with the ground can be estimated based on the multi-axis motion data and/or the translated multi-axis motion data. A fatigue of the user can be estimated based on the amount of time during the stride of the user that the foot of the user is airborne and the amount of time during the stride of the user that the foot of the user is in contact with the ground. A form consistency of the user can be estimated based on the amount of time during the stride of the user that the foot of the user is airborne and/or the amount of time during the stride of the user that the foot of the user is in contact with the ground. A performance of the user can be estimated based on the amount of time during the stride of the user that the foot of the user is airborne and/or the amount of time during the stride of the user that the foot of the user is in contact with the ground. For a given implementation, a sensor platform may be configured to estimate any combination of the foregoing metrics of interest.

Methods described herein can include automatically and/or continuously adjusting measurement/sampling frequency (e.g., with which physiological and/or motion-related measurements are taken) to achieve a required accuracy with minimal power consumption. Alternatively or in addition, methods can include measuring changes in speed and distance without accumulation of large error with passing time by using low-power sensors combined with contextual information and possibly occasional calibration based on context or information from the GPS (i.e., without frequent resort to techniques requiring large amounts of energy).

In some cases, the method can include automatically characterizing the distribution of a user's physiological and/or motion-related metrics, for example to dynamically identify the most appropriate ranges to achieve improvement given the user's current and historical distributions of metrics, and/or to recommend changes in activities appropriate for the user's training, competition, and/or recovery goals.

Methods described herein can include analyzing raw data collected by sensors of the sensor platform to draw inferences, observe trends or patterns, make predictions, and/or create information that is useful to a user. For example, methods described herein can include automatically detecting fatigue by detecting/monitoring changes to athletic form, athletic technique, distributions of physiological state metrics, and/or motion-related patterns of the user. Methods can also include using information about the general and user-specific properties of running and/or walking mechanics to translate acceleration, orientation change, and/or body structure data into the power exerted on the human body by its own muscles and tendons.

Methods described herein estimate the motion and/or positions of users engaging in bipedal motion, and the motion, positions, and orientations of their limbs, with high accuracy over both long and short distance scales and can be implemented in a compact device with a long battery life. For example, for some embodiments described herein, a battery of life of about 6 months can be achieved using two "coin cell" type batteries.

A sensing, signal processing, and feedback system (collectively a "sensing system"), as described herein, can include: (a) one or more sensors, (b) a wireless transceiver, (c) a power source, (d) a microprocessor or microcontroller with associated memory, and (e) a package containing said sensors, transceiver, power source, and microprocessor or microcontroller that is carried or worn by a user, whereby metrics derived from the motion patterns of said user moving under his or her own power are measured and analyzed to provide immediate feedback or store for later use. The package can have any of the following structural features: (a) an arched top, (b) a reinforced bottom plate, (c) weight distribution pillars, (d) flexible potting compound, or (e) resin shock absorbers, so that the durability of said package is increased.

Systems described herein can be configured to calculate one or more of the following metrics and communicate it to the relevant user: (a) force map, (b) impact, (c) ground time, (d) airtime, and (e) efficiency, so that the user can adjust his or her bipedal motion or training behavior in response to this feedback. For example, all of items (a) through (e) may be provided. In other cases, a system can be configured to calculate one or more of the following metrics and communicate it to the relevant user: (f) efficiency, (g) fatigue, (h) consistency, (i) performance, and (j) quality, so that the user can adjust his or her bipedal motion or training behavior in response to this feedback. For example, all of items (0 through (j) may be provided.

The sensor platform and/or the sensing system can be configured to accommodate for drift cancellation, so that the accuracy of location estimation is improved. Alternatively or in addition, the sensor platform and/or the sensing system can be configured to detect an activity (e.g., an activity "type," e.g., running, walking, jumping, dancing, cycling, etc.) based on sensor data collected by the sensor platform, such that a user's activities are classified. Alternatively or in addition, the sensor platform and/or the sensing system can be configured to detect metric values or changes associated with emotional or physical state, and to adjust the feedback that is provided to the user (e.g., adjusting feedback type, format, frequency, etc.) as deemed appropriate for the user's current emotional or physical state.

In some cases, feedback provided to a user can include maps that are automatically derived by the sensing system and/or labeled with information relevant to bipedal motion. Feedback can be automatically triggered based on measurements or calculations by said system. For example, audio feedback can be provided (e.g., including variations in rhythm and tone) based on measurements or calculations by said system. Real-time coaching can be automatically conducted by said system, whereby said user can adjust his or her behavior in response to said coaching. Alternatively or in addition, information can be provided to a coach by the sensing system to enable manual coaching, so that the user can adjust his or her behavior in response to said coaching. Data collected by the sensor platform and/or metrics determined by the sensing system can be shared among said system and other computing systems to enable comparison among users, whereby users may compare said data or metrics with those of other users, to enable collaboration or competition.

Metrics described herein can be measured at one or more locations on said user's body to determine the degree to which said user's motion is asymmetrical. A hardware-software subsystem of the sensing system can support automated registration and activation of the sensing system via the Internet, provide audio and/or visual feedback to said user, and/or control other objects based on measurements and analysis carried out by the sensing system.

A system for sensing and analyzing bipedal motion, as described herein, can be constructed to be durable, provides metrics that are most useful and relevant to athletes, and supports a user interface that is appropriate for day-to-day use.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed.

Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of technology disclosed herein may be implemented using hardware, software, or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (e.g., of designing and making the technology disclosed above) outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the disclosure discussed above. The computer readable medium or media can be transportable, such that the program or programs stored thereon can be loaded onto one or more different computers or other processors to implement various aspects of the present disclosure as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present disclosure need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method, comprising:
measuring, using an IMU of a sensor platform that includes a memory, motion of the sensor platform while the sensor platform is worn by the user engaging in a physical activity to produce multi-axis motion data;
measuring, using a pressure sensor of the sensor platform, an air pressure while the user is engaging in the physical activity to produce air pressure data;
receiving, by a processor, a signal that includes the multi-axis motion data and a signal that includes the air pressure data; and
estimating, by the processor, power expended by the user, based, at least in part, on the air pressure data, a mass of the user, a velocity of the user, a change in a velocity of the user determined from the multi-axis motion data, and a scaling factor, the scaling factor being empirically determined based on measurements of one or more users.

2. The method of claim 1, wherein the scaling factor is a first scaling factor, the method further comprising:
decomposing, by the processor, the multi-axis motion data into horizontal motion components and a vertical motion components, the power expended by the user estimated based, at least in part, on:
the mass of the user, a horizontal velocity of the user, a horizontal change in a velocity of the user, and the first scaling factor divided by a period of time over which the change in the horizontal velocity of the user changed, and
a product of a second scaling factor, the mass of the user, acceleration due to gravity, a change in vertical position the user divided by a period of time over which the vertical position of the user changed.

3. The method of claim 1, further comprising:
estimating a metabolic energy expenditure of the user based on the power expended by the user.

4. The method of claim 1, further comprising:
estimating, by the processor, wind resistance experienced by the user based on the air pressure data, and
wherein estimating the power expended by the user includes accounting for the wind resistance.

5. The method of claim 1, further comprising:
estimating, by the processor, an incline of a path of the user based on the air pressure data and/or the multi-axis motion data, and
wherein estimating the power expended by the user includes accounting for the incline.

6. The method of claim 1, further comprising:
estimating, by the processor, a stride distance of the user based on the multi-axis motion data.

7. The method of claim 1, further comprising:
estimating, by the processor, an amount of time during a stride of the user that a foot of the user is airborne based on the multi-axis motion data; and
estimating, by the processor, an efficiency of the user based on the power expended by the user and the amount of time during the stride of the user that the foot of the user is airborne.

8. The method of claim 1, further comprising:
estimating, by the processor, an amount of time during a stride of the user that a foot of the user is airborne based on the multi-axis motion data; and
estimating, by the processor, an amount of time during the stride of the user that the foot of the user is in contact with the ground based on the multi-axis motion data.

9. The method of claim 8, further comprising:
estimating, by the processor, a fatigue level of the user based on the amount of time during the stride of the user that the foot of the user is airborne and the amount of time during the stride of the user that the foot of the user is in contact with the ground.

10. The method of claim 8, further comprising:
estimating, by the processor, a form consistency of the user based on the amount of time during the stride of the user that the foot of the user is airborne and/or the amount of time during the stride of the user that the foot of the user is in contact with the ground.

11. The method of claim 8, further comprising:
estimating, by the processor, a performance of the user based on the amount of time during the stride of the user that the foot of the user is airborne and/or the amount of time during the stride of the user that the foot of the user is in contact with the ground.

12. The method of claim 1, wherein the IMU includes a gyroscope, the method further comprising:
estimating when the user is airborne based on the multi-axis motion data; and
disabling the gyroscope when the user is airborne.

13. The method of claim 1, further comprising:
varying a sampling rate of the multi-axis motion data based on a comparison of the multi-axis motion data as it is received to the multi-axis motion data stored in the memory.

14. The method of claim 1, wherein:
the multi-axis motion data is received at a first sampling rate; and
orientation data is received from an orientation sensor at a second sampling rate, the method further comprising:
varying the second sampling rate based on the multi-axis motion data.

15. The method of claim 14, wherein varying the second sampling rate comprises:
estimating when the user is airborne based on the multi-axis motion data; and
disabling the orientation sensor when the user is airborne.

16. The method of claim 1, wherein the air pressure data is indicative of variations in altitude and/or wind resistance.

17. The method of claim 1, wherein estimating power expended by the user includes a determination of a contribution of recycled power.

18. The method of claim 1, wherein estimating power expended by the user includes a determination of a running economy coefficient associated with a percentage of metabolic energy transformed into mechanical power output.

19. The method of claim 1, wherein estimating power expended by the user includes:
determining an incline traversed by the user;
determining a contribution of recycled energy associated with the incline; and
determining a running economy coefficient associated with the contribution of recycled energy associated with the incline.

20. The method of claim 1, wherein the one or more users includes the user.

21. The method of claim 1, wherein:
the multi-axis motion data represents motion measured by the IMU in a first reference frame fixed with respect to the sensor platform;
the memory stores orientation data representing an orientation of the sensor platform in a second reference frame fixed with respect to Earth;
the method further comprising:
receiving, by the processor, the orientation data;
translating, by the processor, the multi-axis motion data from the first reference frame to the second reference frame based on the orientation data to yield translated multi-axis motion data; and
decomposing, by the processor, the translated multi-axis motion data into horizontal motion components and vertical motion components in the second reference frame,
the power expended by the user estimated based on the horizontal motion components and vertical motion components.

22. The method of claim 1, further comprising:
applying a low-pass filter to the pressure sensor signal to define a filtered pressure signal; and estimating, by the processor, wind resistance experienced by the user based on the filtered pressure signal, and
estimating the power expended by the user includes accounting for the wind resistance.

23. The method of claim 1, wherein:
the sensor platform further comprises a Global Positioning System (GPS) receiver; and
the velocity of the user determined, in part, based on a signal received from the GPS receiver.

24. The method of claim 1, further comprising generating, by an interface device and during the physical activity, real-time feedback to the user of the power expended by the user, wherein the feedback is provided as at least one of a vibration, a visual output, or an audio output.

25. The method of claim 24, wherein the sensor platform and the interface device are housed within a single device.

26. The method of claim 24, wherein the sensor platform and the interface device are separate devices.

27. The method of claim 24, wherein the interface device is worn or carried by the user during the physical activity.

28. The method of claim 24, wherein the sensor platform is disposed in a housing that contains the processor and a wireless transmitter configured to send an indication of power expended by the user to the interface device.

29. The method of claim 1, wherein the IMU includes at least one of an one-axis accelerometer, a two-axis accelerometer, a three-axis accelerometer, a gyroscope, or a magnetometer.

30. The method of claim 1, wherein estimating power expended by the user is based, at least in part, on a product of the mass of the user, the velocity of the user, the change in the velocity of the user, and the scaling factor divided by a period of time over which the change in the velocity of the first user changed.

* * * * *